United States Patent
Bencini et al.

(10) Patent No.: US 6,619,838 B2
(45) Date of Patent: Sep. 16, 2003

(54) TWO-PIECE SENSOR ASSEMBLY

(75) Inventors: Robert F. Bencini, Sunnyvale, CA (US); Jon Wohlgemuth, Morgan Hill, CA (US); Katie Messing, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 7 days.

(21) Appl. No.: 09/935,380

(22) Filed: Aug. 22, 2001

(65) Prior Publication Data

US 2003/0050558 A1 Mar. 13, 2003

(51) Int. Cl.$^7$ ............................................. G21K 4/00
(52) U.S. Cl. ..................... 378/190; 378/189; 378/204; 378/208
(58) Field of Search ............................. 378/190, 204, 378/208, 189; 250/363.05, 363.08; 600/410, 411, 424, 427, 429, 414, 417

(56) References Cited

U.S. PATENT DOCUMENTS

| 4,941,473 A | 7/1990 | Tenerz et al. |
| 5,386,828 A | 2/1995 | Owens et al. |
| 5,447,156 A | 9/1995 | Dumoulin et al. |
| 5,458,124 A | 10/1995 | Stanko et al. |
| 5,584,296 A | 12/1996 | Cui et al. |
| 5,622,169 A | 4/1997 | Golden et al. |
| 5,709,661 A | 1/1998 | Van Egmond et al. |
| 5,807,258 A | 9/1998 | Cimochowski et al. |
| 5,840,024 A | 11/1998 | Taniguchi et al. |
| 5,868,674 A | 2/1999 | Glowinski et al. |
| 6,106,477 A | 8/2000 | Miesel et al. |

FOREIGN PATENT DOCUMENTS

| EP | 0 468 616 A2 | 1/1992 |
| WO | WO 00/10456 | 3/2000 |

Primary Examiner—Drew A. Dunn
Assistant Examiner—Courtney Thomas
(74) Attorney, Agent, or Firm—Bingham McCutchen LLP

(57) ABSTRACT

A sensor assembly that allows a sensor to be detachably mounted onto a fluoroscopic mount, such as a C-arm, is provided. The sensor assembly includes an electromagnetic sensor that is configured for outputting positional data relating to the fluoroscopic mount. The sensor includes a mount engaging element, and the sensor mount includes a sensor engaging element, both of which are configured to be removably mounted in an interference relationship with each other. The mount engaging element of the sensor can be a sensor housing, or alternatively, an element that is separate from the sensor housing. The sensor mount, which is composed of a non-ferromagnetic material, further includes a spacer for maintaining the sensor a prescribed distance from the ferromagnetic fluoroscopic mount, thereby minimizing any adverse ferromagnetic effects on the sensor.

102 Claims, 18 Drawing Sheets

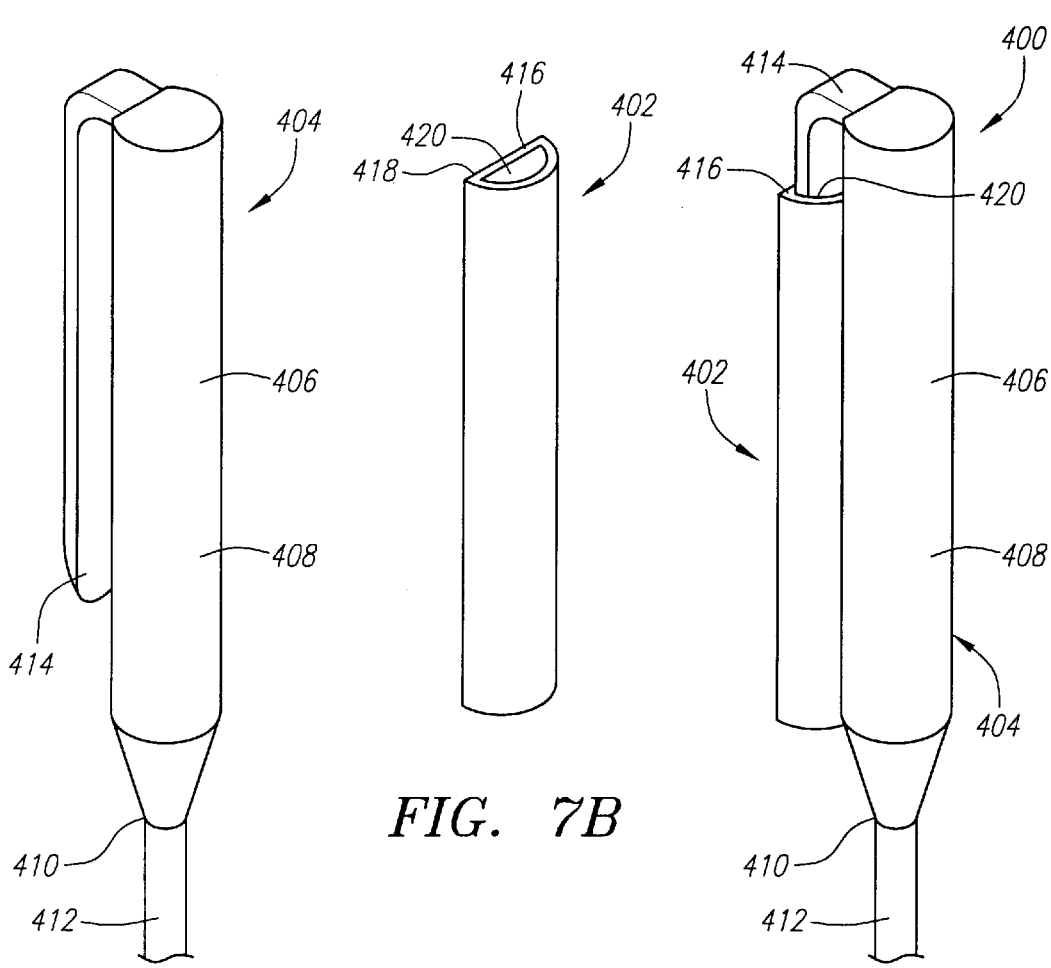
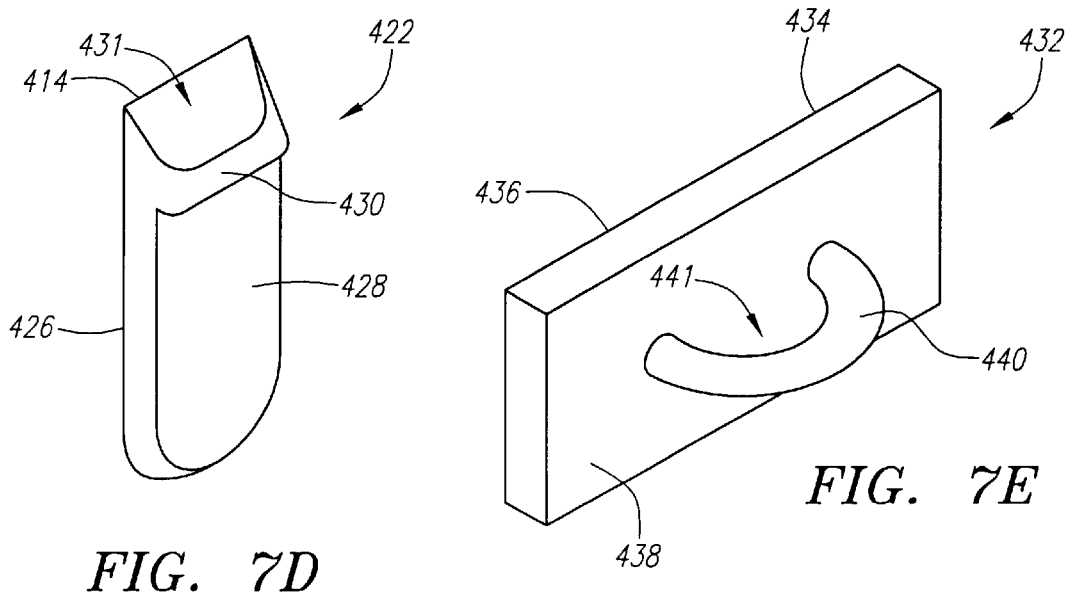
FIG. 7A  FIG. 7B  FIG. 7C  FIG. 7D  FIG. 7E

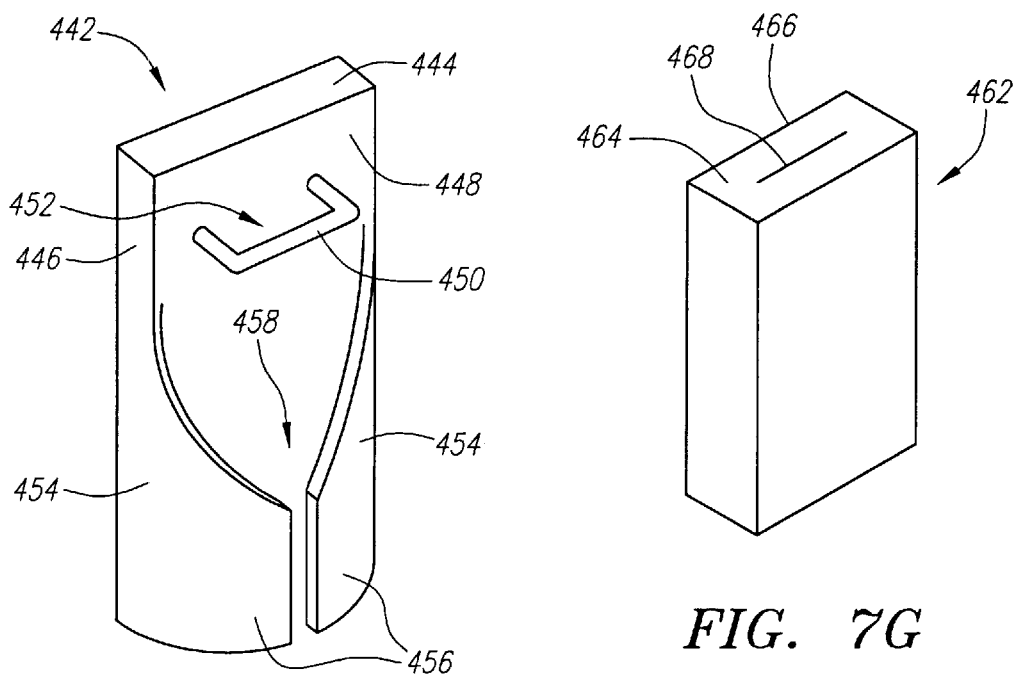
FIG. 7F
FIG. 7G
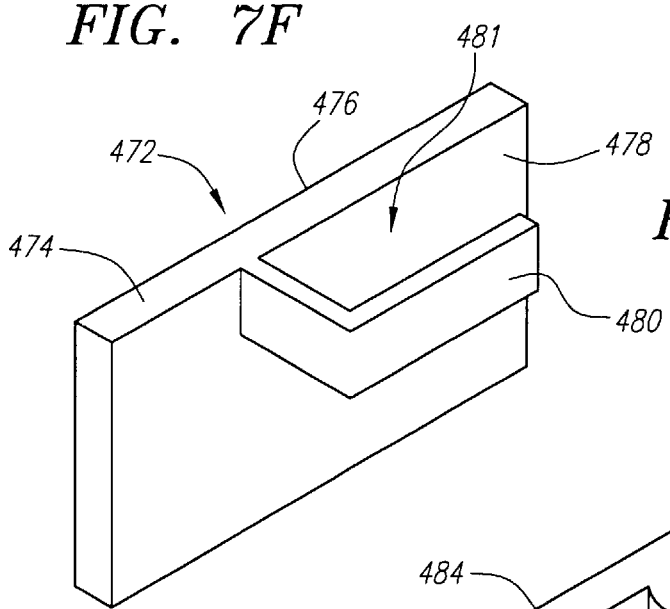
FIG. 7H
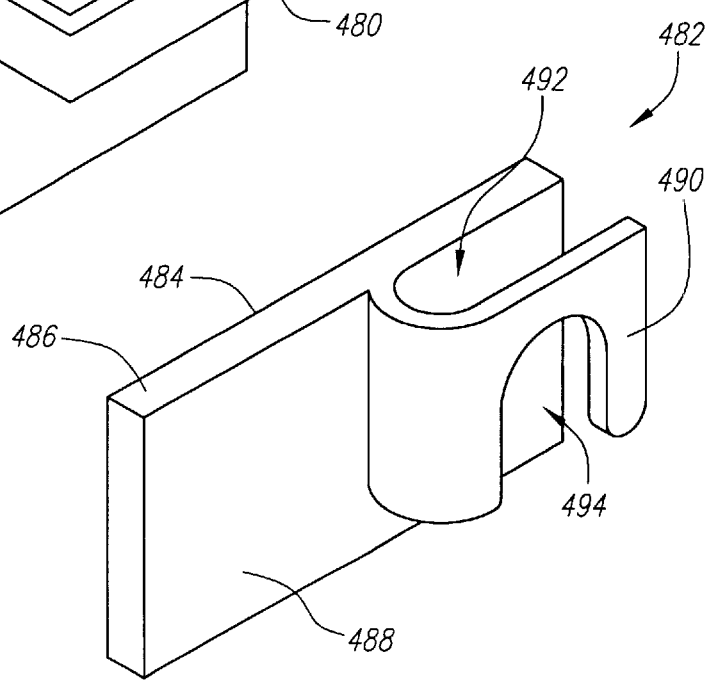
FIG. 7I

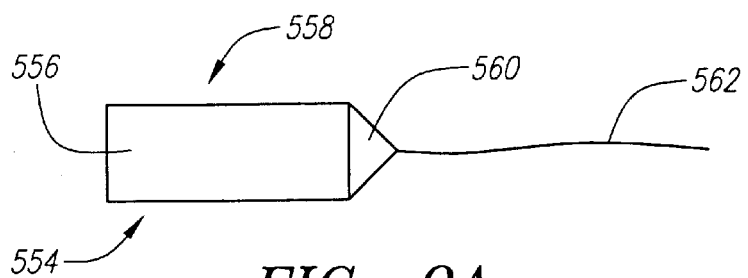
FIG. 9A
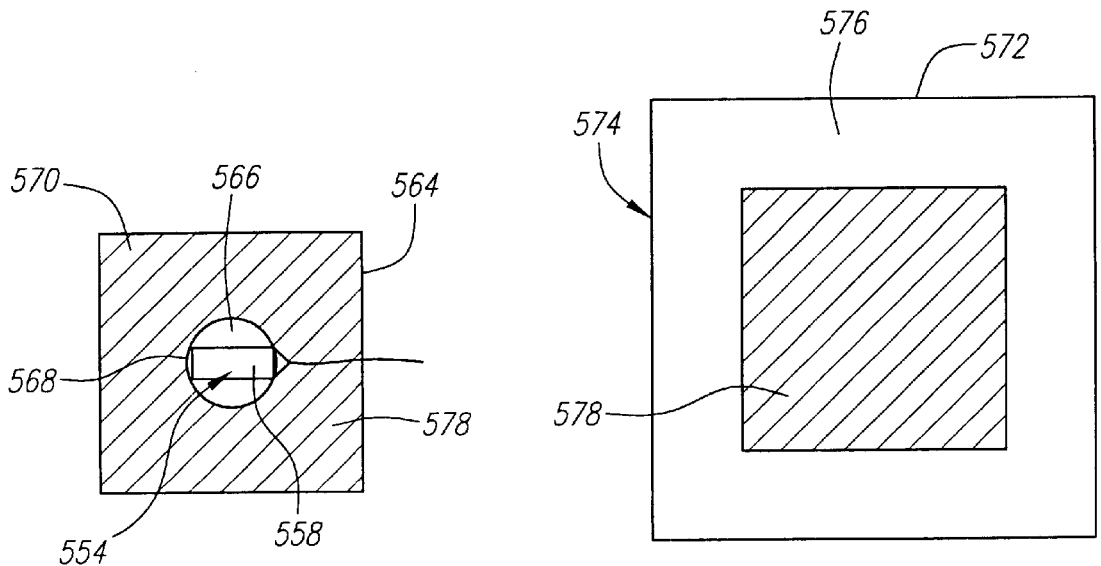
FIG. 9B
FIG. 9C
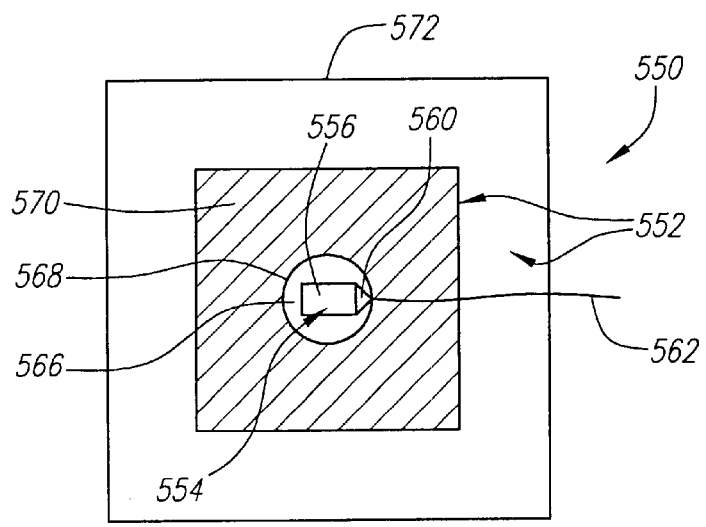
FIG. 9D

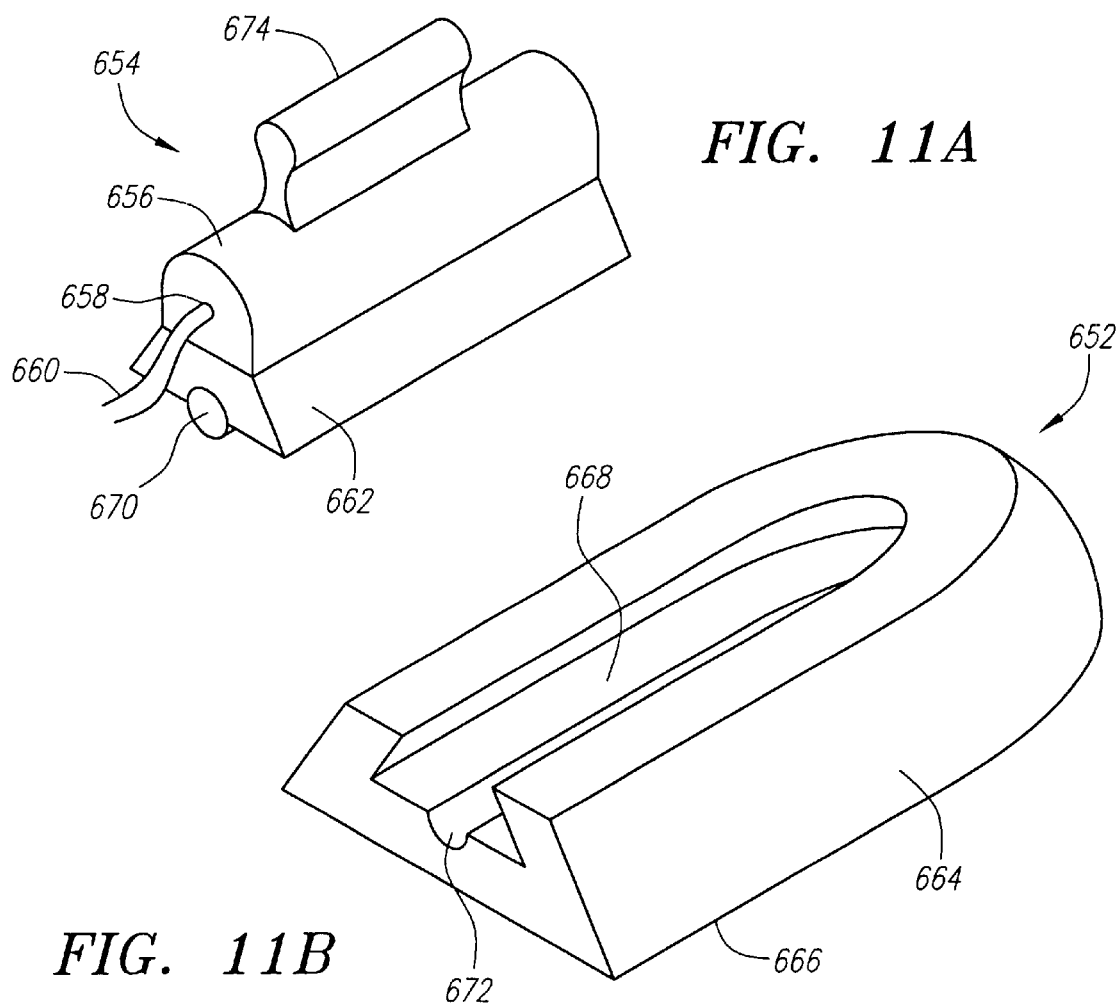
FIG. 11A
FIG. 11B
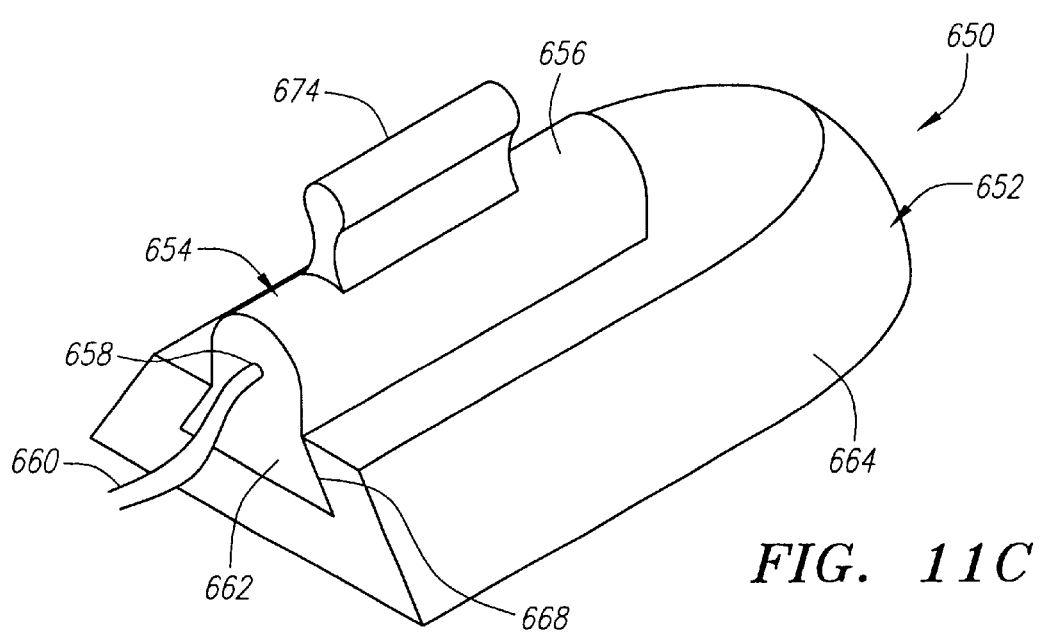
FIG. 11C

TWO-PIECE SENSOR ASSEMBLY

TECHNICAL FIELD OF INVENTION

The present invention relates to an assembly for securely mounting a sensor to an image-acquisition device capable of pivoting, and, in particular for securely mounting a sensor to a C-arm or some other C-shaped fluoroscope.

BACKGROUND OF INVENTION

Referring to FIG. 1, an image-acquisition device 100 can be used for simultaneous real-time image acquisition and intrabody navigation of a probe, such as a catheter 105. Catheters may be employed for diagnostic purposes, e.g., by retrieving samples of tissue, or for therapeutic purposes, e.g., ablation by radiofrequency waves emitted by at least one electrode contained in the catheter. In either case, tracking of the catheter 105 as it is navigated through the body of a patient is of great importance.

To this end, the image-acquisition device 100 comprises a C-arm fluoroscope 110 that may pivot about three orthogonal axes to allow imaging of a patient from several different angles. Typically, such a fluoroscope 110 includes an X-ray source 115 and an image acquisition module 120 mounted on opposite ends of a C-arm 125, as well as a table 130 where the patient lies. The portion of the patient's body being imaged, typically the chest, is positioned between the ends of the C-arm 125. The image-acquisition module 120 converts x-rays that transit through the patient on the table 130 into electronic signals representative of 2-D images of the patient. The pivotable feature provides images from various perspectives, thereby allowing the reconstruction of a 3-D image of the patient from a series of successive 2-D images. This function is performed by a controller/processor 135, which is coupled to the image-acquisition module 120.

Tracking of the catheter 105 is accomplished by using a fixed transmitter 140 to transmit to a sensor 145 located on the catheter 105, thereby locating the catheter 105 relative to the transmitter 140. Optionally, a reference sensor can be placed on the patient, preferably the chest, to create a "fixed" space in combination with the transmitter 140 relative to other moving sensors. In this manner, the device 100 compensates for any movement of the patient, such as chest movement during the respiratory cycle. The sensor 145 typically comprises a housing that contains three pairs of electromagnetic sensing elements for the three orthogonal axes. In any event, the continuously changing position and orientation of the catheter 105 can be inferred from the electromagnetic signals transmitted by the transmitter 140 and received by the sensor 145. This tracking function is performed by driving circuitry 150 and reception circuitry 155, which are respectively coupled to the transmitter 140 and sensor 145, and the controller/processor 135, which controls the driving circuitry 150 and processes the signals received by the reception circuitry 155.

Thus, by determining the position and orientation of the catheter 105 relative to the frame of reference defined by the transmitter 140 and the optional reference sensor, the controller/processor 135 determines the position and orientation of the catheter 105 relative to the 2-D image acquired by the fluoroscope 110. The controller/processor 135 then synthesizes a combined image that includes both the 3-D image of the patient and an icon representing the catheter 105 positioned and oriented with respect to the 3-D image, and then displays this combined image on a monitor 158. In order to synchronize the acquired location of the catheter 105 with each 2-D image, the orientation of which changes as the C-arm 125 is rotated around the patient, another sensor 160, which is similar to the sensor 145 located in the catheter 105, is mounted on the C-arm 125. Electromagnetic signals received by the sensor 160 from the transmitter 140 are sent to reception circuitry 165, which is identical to the reception circuitry 155. The controller/processor 135 is coupled to this reception circuitry 155 and acquires the data therefrom to determine the orientation of the C-arm 125, and thus the orientation of the 2-D image, at any given time, so as to provide a means to synchronize the image of the catheter 105 with that of each 2-D image. Further details on the image-acquisition device 105 are described in PCT publication WO 00/10456, entitled "Intrabody Navigation System for Medical Applications," and published on Mar. 2, 2000, which publication is fully and expressly incorporated herein by reference.

In order to securely mount the sensor 160 to the C-arm 125, certain constraints must be considered. First, as the sensor 160 serves as a fixed point of reference, it must be sufficiently secured to the C-arm 125, such that it does not move relative to the C-arm 125 when the C-arm 125 pivots. The sensor 160, however, should be easily engageable and disengageable from the C-arm 125 in order to replace the sensor 160 if desired. Secondly, as the sensor 160 functions by the reception of electromagnetic waves, it must not contact or be placed in proximity to any ferromagnetic material, such as steel or any other material or alloy containing iron, which would disrupt the magnetic field of the sensor 160.

Thus, an objective of this invention is to provide for a sensor assembly that detachably secures the sensor onto a C-arm, or some other pivotable image-acquisition device, without disrupting the sensor's magnetic field.

SUMMARY OF THE INVENTION

The present inventions are directed to medical sensor assemblies that include sensors that can be detachably mounted onto a fluoroscopic mount, such as a C-arm. In accordance with a general aspect of the present inventions, a medical sensor assembly for use with a fluoroscopic mount comprises an electromagnetic sensor that is configured for outputting positional data relating to the fluoroscopic mount. The sensor includes a mount engaging element, and the sensor mount includes a sensor engaging element, both of which are configured to be removably mounted in an interference relationship with each other. The mount engaging element of the sensor can be a sensor housing, or alternatively, an element that is separate from the sensor housing. The sensor mount, which is composed of a non-ferromagnetic material, further includes a spacer for maintaining the sensor at a prescribed distance from the ferromagnetic fluoroscopic mount, thereby minimizing any adverse ferromagnetic effects on the sensor.

The sensor mount may be configured, e.g., in a front-mount arrangement, such that the sensor is mounted to the sensor mount in a direction perpendicular to the plane in which the sensor mount is mounted to the fluoroscopic mount. Alternatively, the sensor mount may be configured, e.g., in a side-mount arrangement, such that the sensor is mounted to the sensor mount in a direction parallel to the plane in which the sensor mount is mounted to the fluoroscopic mount.

The spacer can be configured to be permanently mounted to the fluoroscopic mount, e.g., by bonding or welding thereto. In this case, the sensor engaging element of the sensor mount can be permanently mounted to the spacer. For example, the sensor engaging element can be bonded or welded thereto, or can be formed with the spacer as a unibody structure. Thus, the sensor with the mount engaging element can be repeatedly attached to and detached from the fluoroscopic mount. Alternatively, the sensor engaging element, rather than the spacer, is configured to be permanently mounted to the fluoroscopic mount, e.g., by bonding or welding thereto. In this case, the spacer acts as the mount engaging element, in that it is configured to be removably mounted to the sensor engaging element, e.g., by using a hook-in-loop material, such as Velcro®. The mount engaging element of the sensor can be permanently mounted to the spacer, e.g., by bonding or welding thereto. Thus, the sensor with the spacer can be repeatedly attached to and detached from the fluoroscopic mount.

In accordance with particular aspects of the present inventions, the sensor engaging element and mount engaging element may be variously designed. For example, the sensor engaging element of the sensor mount may comprise a pair of arms, and the mount engaging element of the sensor may comprise the sensor housing, which is received between the pair of arms in a snug relationship. As another example, the sensor engaging element may comprise a pair of arms, and the mount engaging may comprise a T-shaped housing that has a shaft configured to be inserted between the pair of arms and a pair of oppositely-extending sensor arms that are configured to be respectively disposed on the pair of arms. As still another example, the sensor engaging element may be an open cavity, and the mount engaging element may be a sensor housing or other member that can be received within the cavity in a direction perpendicular to a plane in which the sensor mount is mounted. As still another example, the sensor engaging element may be a conical cavity, and the mount engaging element may be a conical sensor housing that is received by the conical cavity. As still another example, the sensor engaging element may comprise means for receiving a clip, and the mount engaging element may comprise a clip that is received by the clip receiving means. As still another example, the sensor engaging element may comprise one of a cavity and member, and the mount engaging element may comprise the other of the cavity and member, with the cavity and member having substantially uniform and matching cross-sections, such that they can slidingly engage each other. As still another example, the sensor engaging element may comprise one of a snap protuberance and hole, and the mount engaging element may comprise the other of the snap protuberance and hole, with the protuberance and hole being capable of engaging each other in a snap-fit arrangement. As still another example, the sensor engaging element may comprise a flexible planar member, e.g., a hook-in-loop material, and the mount engaging element may comprise a rigid planar member, with the flexible planar member being configured to mount the rigid planar member to the sensor mount.

BRIEF DESCRIPTION OF THE DRAWINGS

In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings.

FIG. 3 depicts one embodiment of the sensor assembly of the present invention. In particular.

FIG. 4 depicts another embodiment of the sensor assembly of the present invention. In particular.

FIG. 5 depicts still another embodiment of the sensor assembly of the present invention. In particular.

FIG. 6 depicts another embodiment of the sensor assembly of the present invention. In particular.

FIG. 7 depicts another embodiment of the sensor assembly of the present invention. In particular, FIG. 7A depicts a perspective view of a sensor; FIG. 7B depicts a perspective view of a sensor mount for use with the sensor of FIG. 7A; FIG. 7C depicts a perspective view of the sensor of FIG. 7A mounted in the sensor mount of FIG. 7B; and FIGS. 7D–7I depict perspective views of alternate sensor mounts for use with the sensor of FIG. 7A.

FIG. 8 depicts still another embodiment of the sensor assembly of the present invention. In particular.

FIG. 9 depicts another embodiment of the sensor assembly of the present invention. In particular, FIG. 9A depicts an elevation view of a sensor; FIG. 9B depicts an elevation view of a portion of a sensor mount in which the sensor of FIG. 9A is mounted; FIG. 9C depicts an elevation view of the other portion of the sensor mount for use with the sensor of FIG. 9A; and FIG. 9D depicts an elevation view of the sensor of FIG. 9A mounted in the sensor mount of FIGS. 9B and 9C.

FIG. 10 depicts still another embodiment of the sensor assembly of the present invention. In particular.

FIG. 11 depicts still another embodiment of the sensor assembly of the present invention. In particular, FIG. 11A depicts a perspective view of a sensor; FIG. 11B depicts a perspective view of a sensor mount for use with the sensor of FIG. 11A; and FIG. 11C depicts a perspective view of the sensor of FIG. 11A mounted in the sensor mount of FIG. 11B.

FIG. 12 depicts still another embodiment of the sensor assembly of the present invention. In particular.

FIG. 13 depicts still another embodiment of the sensor assembly of the present invention. In particular.

FIG. 14 depicts still another embodiment of the sensor assembly of the present invention. In particular.

FIG. 15 depicts still another embodiment of the sensor assembly of the present invention. In particular.

FIG. 16 depicts still another embodiment of the sensor assembly of the present invention. In particular.

FIG. 17 depicts still another embodiment of the sensor assembly of the present invention. In particular.

FIG. 18 depicts still another embodiment of the sensor assembly of the present invention. In particular.

DETAILED DESCRIPTION OF THE PREFERRED EMBODIMENTS

Figure 2:
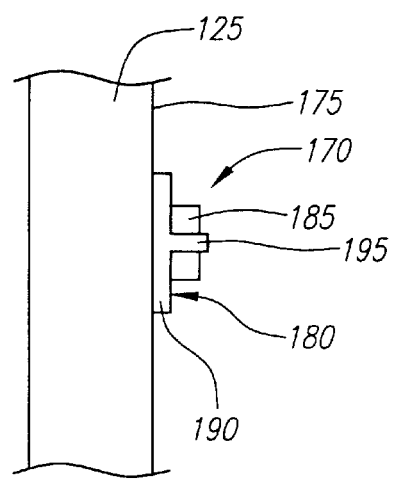
FIG. 2 depicts a conceptual drawing of a sensor assembly of the present invention.

The present inventions provide for a removable sensor assembly for tracking a movable object, such as a catheter, within a patient's body. As illustrated in FIG. 2, a sensor assembly 170 constructed in accordance with the present inventions is used with the afore-described image acquisition device 105 to facilitate synchronization of the catheter icon with the 2D fluoroscopic images while the C-arm 125 rotates about the patient. The sensor assembly 170 is shown mounted on a lateral surface 175 of the C-arm 125 near the upper end thereof. The sensor assembly 170, however, may be mounted at alternative positions along the lateral surface, or any surface, of the C-arm 125, as long as it is provides a reference point that accurately represents the relative position and orientation of the C-Arm 125.

Figure 1:
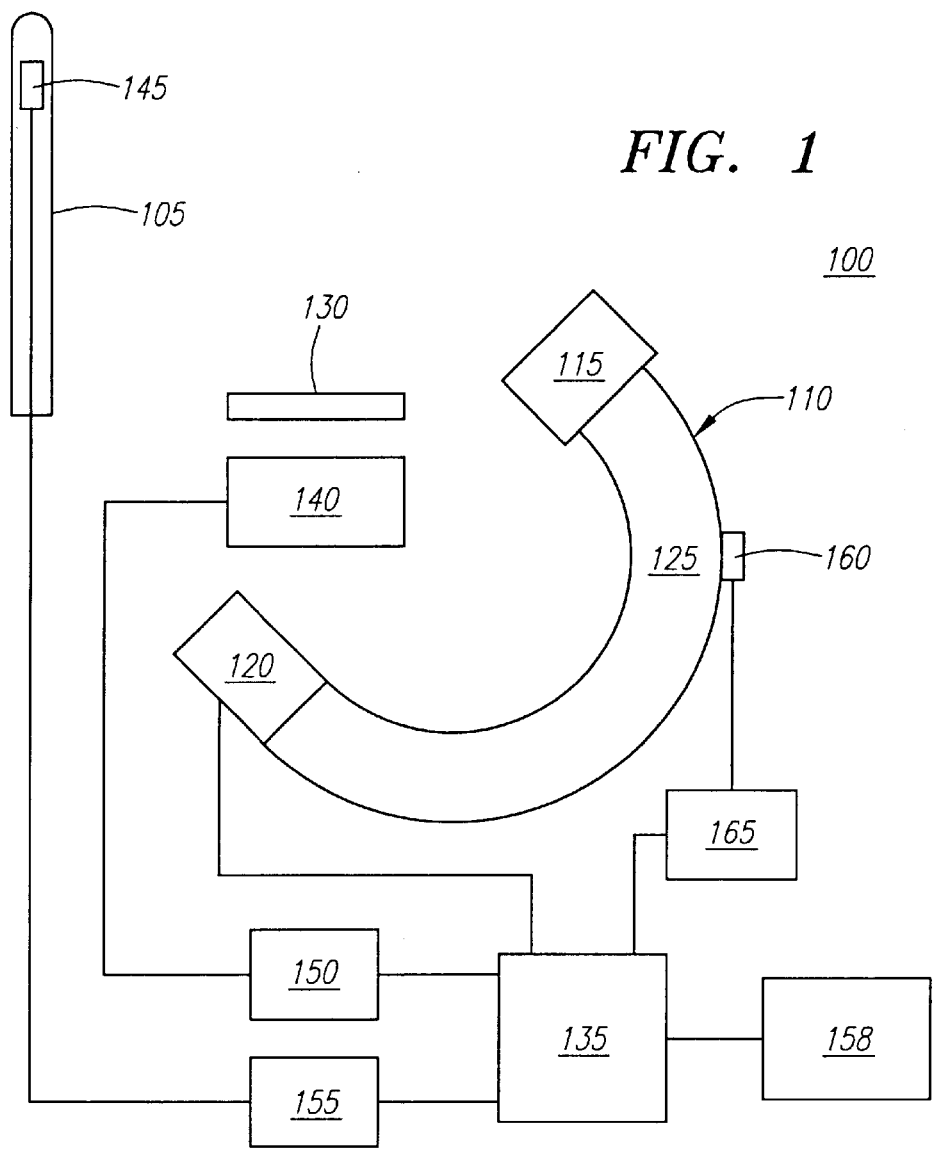
FIG. 1 depicts a lateral elevation view of a C-arm with the sensor assembly of the present invention secured thereto.

As illustrated in FIG. 2, the sensor assembly 170 comprises a sensor mount 180, which is permanently attached to C-arm 125, and a sensor 185, which is removably attached to the sensor mount 180. In the illustrated embodiment, the sensor 185 comprises a housing that contains three pairs of sensing elements (not depicted), which orthogonally sense electromagnetic energy in three axes. The sensor 185 also includes an outlet (not depicted) for the leads or wires that connect to the reception circuitry 155 and controller/processor 135 (depicted in FIG. 1).

The sensor mount 180 is permanently attached to a mounting surface 175 of the C-arm 125 by known means, such as by being welded, bonded, or even screwed on. The sensor mount 180 is made of non-ferromagnetic material, i.e., anything other than steel or a natural or synthetic material containing iron, and acts to separate and provide an appropriate, prescribed distance between the sensor 185 and the mounting surface 175 of the ferromagnetic C-arm 125, thereby preventing an adverse magnetic effect on the sensor 185. To this end, the sensor mount 180 includes a spacer 190, the thickness of which defines the distance between the sensor 185 and the mounting surface of the C-arm 125. The sensor mount 180 further comprises a sensor engaging element 195 with which the sensor 185 mates and is secured by an interference fit. The element of the sensor 185 that the sensor engaging element 195 of the sensor mount 80 engages is, for the purposes of this specification, a mount engaging element, which may be a sensor housing or other element. For the purposes of this specification, an interference fit refers to any fit or contact between mating parts having prescribed limits of size, material, and shape, so that a reversible mechanical hold between the mating parts is established.

As will be understood by the following description and reference to the respective drawings, the present inventors have developed a variety of innovative sensor mount assemblies with removably attached sensors that are maintained at the required distance from the surface of the C-arm 125.

Figure 3A:
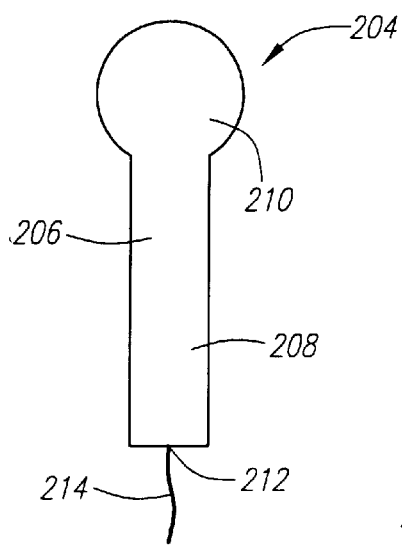
FIG. 3A depicts an elevation view of a sensor.
Figure 3B:
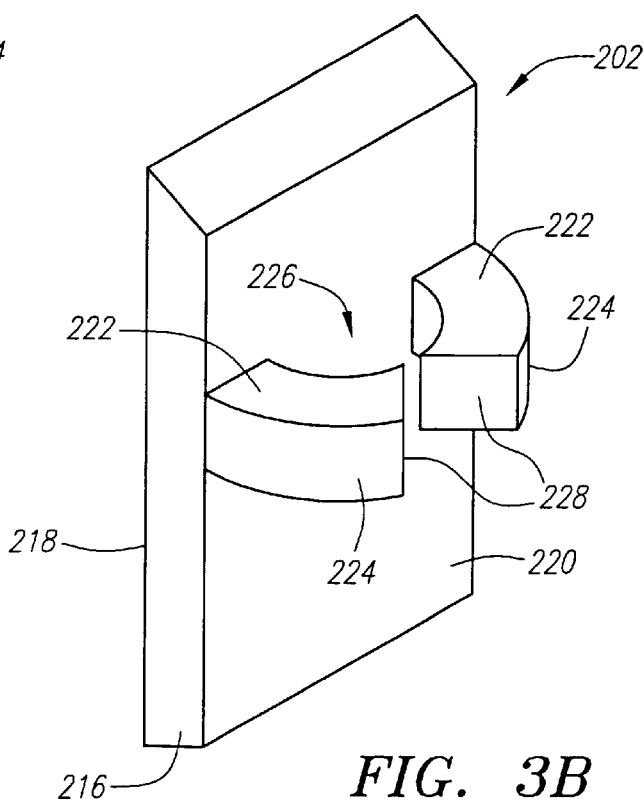
FIG. 3B depicts a perspective view of a preferred sensor mount for use with the sensor of FIG. 3A.
Figure 3C:
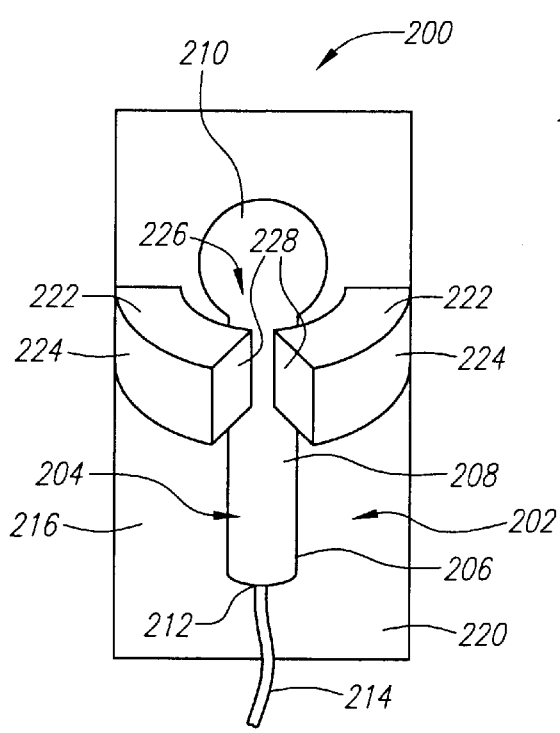
FIG. 3C depicts an elevation view of the sensor of FIG. 3A mounted in the sensor mount of FIG. 3B.

Referring now to FIG. 3C, a preferred embodiment of a sensor assembly 200 is depicted. The sensor assembly 200 comprises a sensor mount 202 (shown separately in FIG. 3B) and a sensor 204 (shown separately in FIG. 3A), which is removably attached to the sensor mount 202. The sensor 204 comprises a sensor housing 206, which contains sensing elements (not depicted). The sensor housing 206 has a substantially tubular shaft 208 that includes an outlet 212 at one end from which sensor wires 214 extend, and an oppositely-disposed rounded end 210. As can be seen, the diameter of the rounded end 210 is greater than the diameter of the shaft 208.

The sensor mount 202 comprises a planar spacer flange 216, which spaces the mounted sensor 204 the required distance away from the C-arm 125. To this end, the spacer flange 216 comprises a first planar mounting surface 218, which is the surface used to permanently attach the sensor mount 202 to the C-arm 125 via suitable means, such as welding or bonding, and an oppositely-disposed second planar mounting surface 220 from which a pair of sensor holding arms 222 extend. The ends 224 of the arms 222 curve towards each other to define an aperture 226 that has a cross-section that substantially matches that of the shaft 208 of the sensor housing 206, such that the sensor 204 is disposed within the aperture 226 in a snap-fit arrangement with the arms 222. Thus, as best illustrated in FIG. 3C, the shaft 208 of the sensor housing 206 fits snugly within the aperture 226, with the round end 210 of the sensor housing 206 abutting the tops of the arms 222. It should be noted that the sensor mount 202 can be considered a front mount in that the sensor 204 is inserted therein in a direction perpendicular to the first planar mounting surface 220.

The ends 224 of the arms 222 comprise beveled edges 228, which guide and facilitate the insertion of the sensor housing shaft 208 between the ends 224 of the arms 222 and into aperture 226. Moreover, the beveled edges 228 allow the arms 222 to almost completely enclose the sensor housing shaft 208, thereby providing a more secure fit between the sensor mount 202 and sensor 204. Preferably, the arms 222 are composed of a firm material having an elastic property, such as an elastomer, so that their shape may be distorted as the shaft 208 is being inserted therebetween, yet at least partially restored once inserted.

Figure 3D:
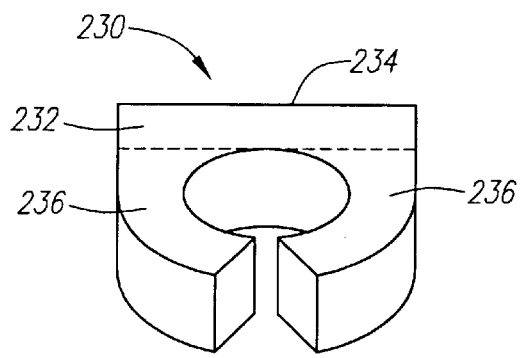
FIGS. 3D and 3E are perspective views of alternative sensor mounts for use with the sensor of FIG. 3A.
Figure 3E:
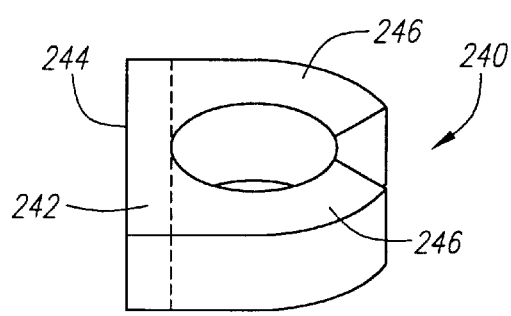

FIGS. 3D and 3E depict alternative embodiments of sensor mounts that are similar to the afore-described sensor mount 202, with the exception that they include spacer flanges that are coextensive with the pair of sensor holding arms, i.e., the pair of sensor holding arms has the same profile as the spacer flange when viewing the mount at an angle perpendicular to the mounting surface of the mount. In particular, FIG. 3D depicts a front sensor mount 230 that comprises a spacer flange 232 (set off by dashed lines) that includes a mounting surface 234 for mounting of the sensor mount 230 to the C-arm 125, and a pair of arms 236 that extend from the flange 232 in a direction perpendicular to the mounting surface 234. As can be seen, the arms 236 have the same profile as the spacer flange 232 when viewing it at an angle perpendicular to the mounting surface 234. FIG. 3E depicts a side sensor mount 240 that comprises a spacer flange 242 (set off by dashed lines) that includes a mounting surface 244 for mounting of the sensor mount 240 to the C-arm 125, and a pair of arms 246 that extend from the flange 242 in a direction parallel to the mounting surface 244. As can be seen, the arms 246 have the same profile as the spacer flange 242 when viewing it at an angle perpendicular to the mounting surface 244.

Figure 4A:
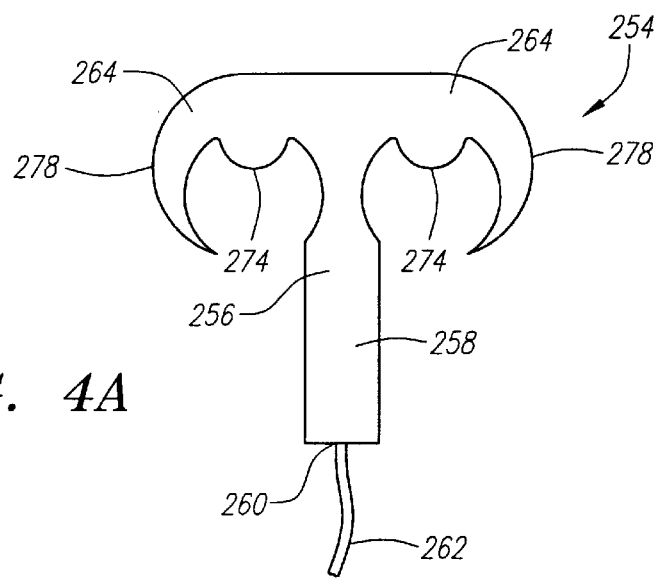
FIG. 4A depicts an elevation view of a sensor.
Figure 4B:
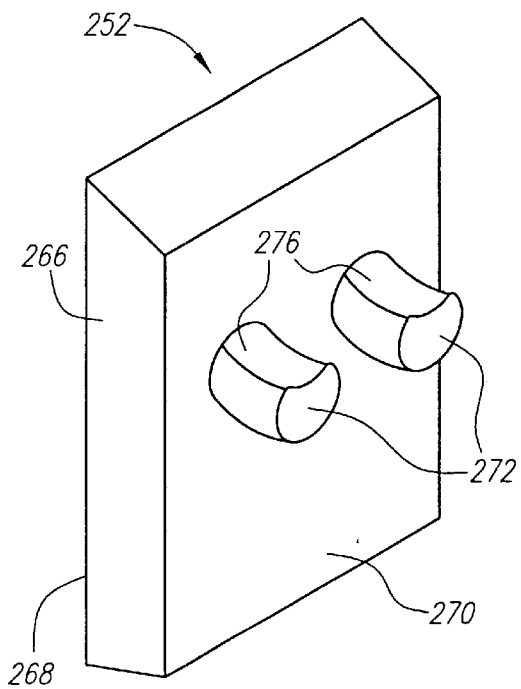
FIG. 4B depicts a perspective view of a sensor mount for use with the sensor of FIG. 4A.
Figure 4C:
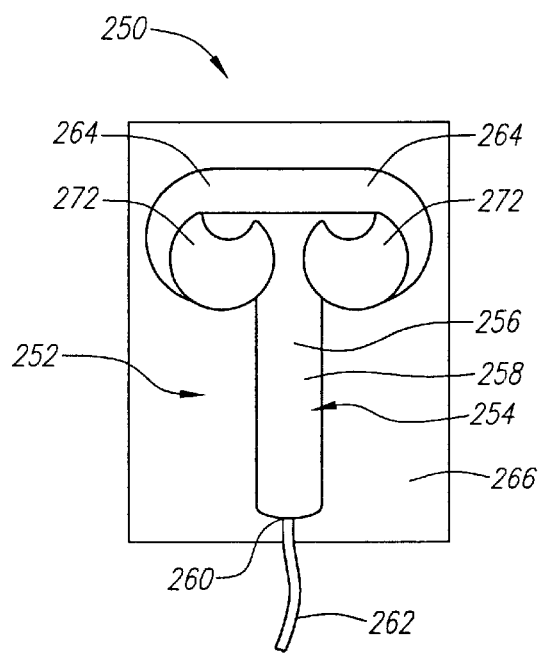
FIG. 4C depicts an elevation view of the sensor of FIG. 4A mounted in the sensor mount of FIG. 4B.

Referring to FIGS. 4A–4C, another preferred embodiment of a sensor assembly 250 is depicted. The sensor assembly 250 comprises a sensor mount 252 (shown separately in FIG. 4B) and a sensor 254 (shown separately in FIG. 4A), which is removably attached to the sensor mount 252. The sensor 254 comprises a T-shaped sensor housing 256, which contains sensing elements (not depicted). The sensor housing 256 has a substantially tubular shaft 258 that includes an outlet 260 at one end from which sensor wires 262 extend, and a pair of sensor arms 264 at the other end. As illustrated, the pair of sensor arms 264 extend perpendicularly from the shaft 258 in opposite directions and in a coplanar relationship with the shaft 258. The sensor arms 264 also include ends 278 that curve towards the shaft 258 for reasons that will further be described below.

The sensor mount 252 comprises a planar spacer flange 266, which spaces the mounted sensor 254 the required distance away from the C-arm 125. To this end, the spacer flange 266 comprises a first planar mounting surface 268, which is the surface used to permanently attach the sensor mount 252 to the C-arm 125 via suitable means, such as welding or bonding, and an oppositely-disposed second planar mounting surface 270 from which a pair of sensor holding arms 272 perpendicularly extend.

The sensor arms 264 can be removably attached to the sensor holding arms 272 in a snap-fit arrangement. To this end, the sensor arms 264 each includes a ridge 274, and the sensor holding arms 272 each includes an indentation 276. Alternatively, the sensor arms 264 can each include an indentation, and the sensor holding arms 272 can each include a ridge. In any event, the sensor arms 264 and sensor holding arms 272 include features that facilitate the snap-fit arrangement. Thus, when the sensor shaft 258 is disposed between the sensor holding arms 272, and the sensor arms 264 are disposed on the sensor holding arms 272 as illustrated in FIG. 4C, the ridges 274 snap into the indentations 276 to provide a secure fit between the sensor 254 and the sensor mount 252. Additionally, the respective ends 278 of the sensor arms 264 engage the sensor holding arms 272 to more securely fit the sensor 254 and sensor mount 252.

Figure 5A:
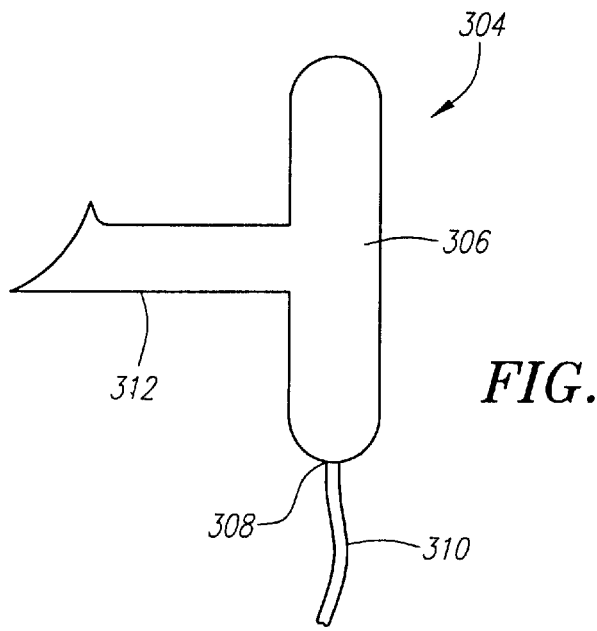
FIG. 5A depicts a lateral elevation view of a sensor.
Figure 5B:
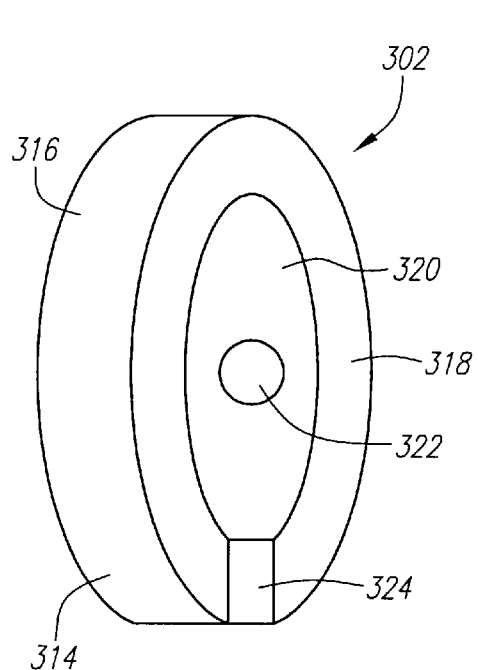
FIG. 5B depicts a perspective view of a sensor mount for use with the sensor of FIG. 5A.
Figure 5C:
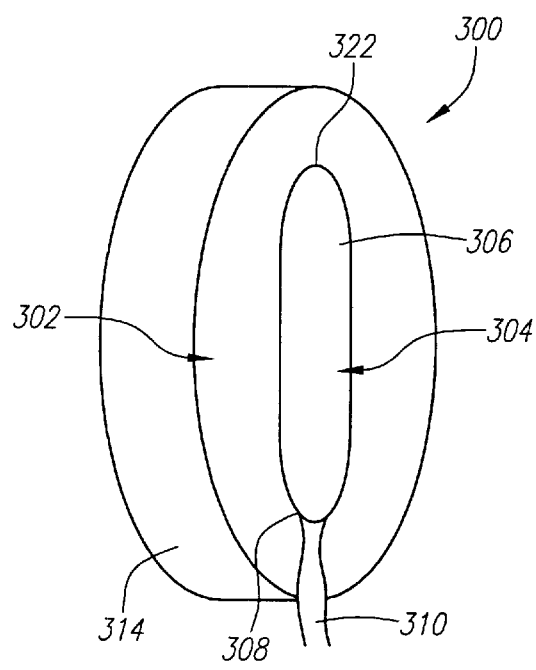
FIG. 5C depicts a perspective view of the sensor of FIG. 5A mounted in the sensor mount of FIG. 5B.

Referring to FIGS. 5A–5C, still another preferred embodiment of a sensor assembly 300 is depicted. The sensor assembly 300 comprises a sensor mount 302 (shown separately in FIG. 5B) and a sensor 304 (shown separately in FIG. 5A), which is removably attached to the sensor mount 302. The sensor 304 comprises an oblong sensor housing 306, which contains sensing elements (not depicted). The sensor housing 306 has an outlet 308 at one end from which sensor wires 310 extend. The sensor housing 306 further comprises a barb 312 that extends perpendicularly from its center. Alternatively, the barb 312 may extend from any longitudinal point on the sensor housing 306.

The sensor mount 302 comprises a planar spacer flange 314, which spaces the mounted sensor 304 the required distance away from the C-arm 125. To this end, the spacer flange 314 comprises a first planar mounting surface 316, which is the surface used to permanently attach the sensor mount 302 to the C-arm 125 via suitable means, such as welding or bonding, and an oppositely-disposed second planar mounting surface 318, in which an open oblong cavity 320 is formed for receiving the sensor housing 306. The open cavity 320 includes a hole 322 along its midpoint for receiving the barb 312 of the sensor housing 306. In this regard, the sensor housing 306 can be removably mounted within the open cavity 320 in a direction perpendicular to the first planar mounting surface 316 by disposing the barb 312 within the hole 322, as illustrated in FIG. 5C. To further facilitate the mounting of the sensor 304 on the sensor mount 302, the shape and size of the sensor housing 306 and open cavity 320 are similar, such that the sensor housing 306 is securely fit within the open cavity 320. Alternatively, the spacer flange 314 may be composed of an elastic material, and the size of the cavity 320 may be slightly smaller than the size of the housing 306, such that the cavity 320 expands in a gripping relationship with the inserted housing 306. Furthermore, a channel 324 is formed within the second planar mounting surface 318 of the spacer flange 314 to receive the sensor wires 310.

Figure 6A:
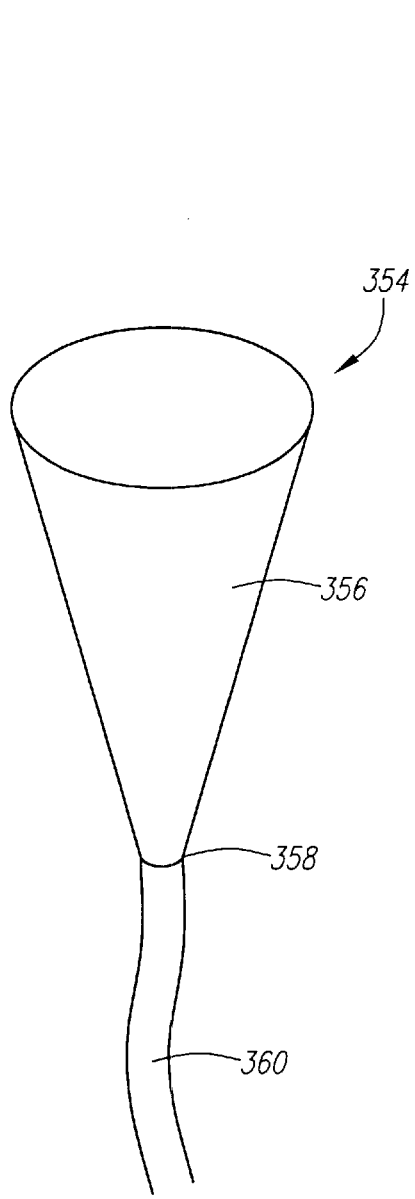
FIG. 6A depicts a perspective view of a sensor.
Figure 6B:
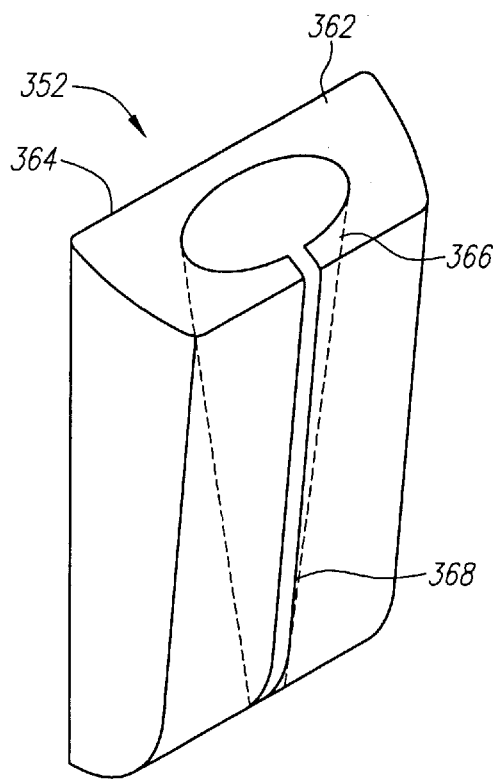
FIG. 6B depicts a perspective view of a sensor mount for use with the sensor of FIG. 6A.
Figure 6C:
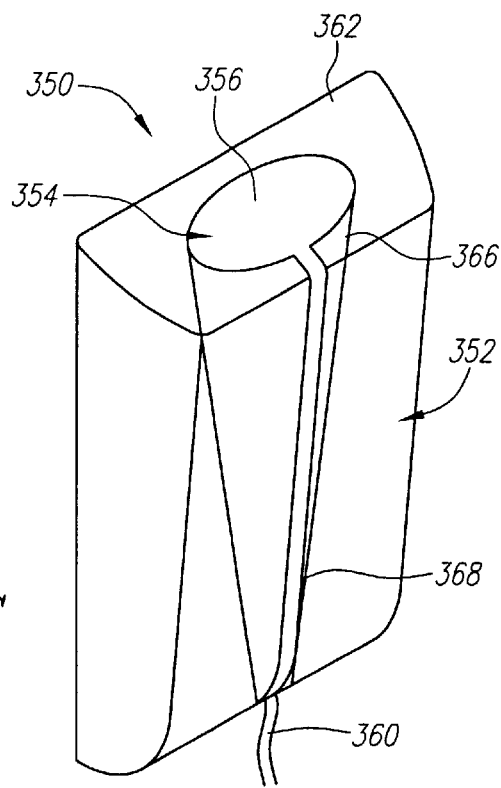
FIG. 6C depicts a perspective view of the sensor of FIG. 6A mounted in the sensor mount of FIG. 6B.

Referring to FIGS. 6A–6C, still another preferred embodiment of a sensor assembly 350 is depicted. The sensor assembly 350 comprises a sensor mount 352 (shown separately in FIG. 6B) and a sensor 354 (shown separately in FIG. 6A), which is removably attached to the sensor mount 352. The sensor 354 comprises a conical sensor housing 356, which contains sensing elements (not depicted). The sensor housing 356 has an outlet 358 at one end from which sensor wires 360 extend. The sensor mount 352 comprises a spacer flange, which spaces the mounted sensor 354 the required distance away from the C-arm 125. To this end, the spacer flange 362 comprises a mounting surface 364, which is the surface used to permanently attach the sensor mount 352 to the C-arm 125 via suitable means, such as welding or bonding. The spacer flange 362 further comprises a conical cavity 366 for receiving the conical sensor housing 356.

In this regard, the conical sensor housing 356 can be removably mounted within the conical cavity 366 in a parallel direction to the mounting surface 364, as illustrated in FIG. 6C. To ensure a tight fit between the sensor 354 and the sensor mount 352, the spacer flange 362 is preferably composed of an elastic material, and the size of the conical cavity 366 is slightly smaller than the size of the conical housing 356, such that the conical cavity 366 expands in a gripping relationship with the inserted conical housing 356. The spacer flange 362 further includes a slit 368 for receiving the sensor wires 360. As illustrated, the slit 368 extends from the conical cavity 364 to the exterior of the spacer flange 362, and is oriented in a direction parallel to the axis of the open cavity 364.

Referring now to FIGS. 7A–7C, still another preferred embodiment of a sensor assembly 400 is depicted. The sensor assembly 400 comprises a sensor mount 402 (shown separately in FIG. 7B) and a sensor 404 (shown separately in FIG. 7A), which is removably attached to the sensor mount 402. The sensor 404 comprises a sensor housing 406, which contains sensing elements (not depicted). The sensor housing 406 has a substantially tubular shaft 408 that includes an outlet 410 at one end from which sensor wires 412 extend, and a clip 414 at the opposite end. The clip 414 exhibits a non-circular cross-section, which in the illustrated embodiment, is generally D-shaped.

The sensor mount 402 comprises a spacer flange 416, which spaces the mounted sensor 404 the required distance away from the C-arm 125. To this end, the spacer flange 416 comprises a planar mounting surface 418, which is the surface used to permanently attach the sensor mount 402 to the C-arm 125 via suitable means, such as welding or bonding. The sensor mount 402 also comprises clip-receiving means 420, and specifically a cavity that exhibits a non-circular cross section, which in the illustrated embodiment, is D-shaped. As illustrated in FIG. 7C, the cavity 420 snugly receives the clip 414 in a direction parallel to the planar mounting surface 418.

FIGS. 7D–7F depict alternative embodiments of sensor mounts that are similar to the afore-described sensor mount 402, with the exception that the means for receiving the clip 414 comprises a handle that is formed on the spacer flange. Specifically referring to FIG. 7D, a sensor mount 422 comprises a spacer flange 424 that includes a first planar mounting surface 426 for permanently mounting the sensor mount 422 to the C-arm 125, and a second planar mounting surface 428 from which a handle 430 extends. The handle 430 forms an aperture 431 between it and the second planar surface 428 for receiving the clip 414 of the sensor housing 406 in a direction parallel to the first planar mounting surface 426. In the illustrated embodiment, the aperture 431 exhibits a cross-section substantially matching that of clip 414, and in this case a D-shaped cross-section, so that the handle 430 snugly holds the clip 414. The length of the spacer flange 424 preferably approximately matches that of the clip 414.

Specifically referring to FIG. 7E, a sensor mount 432 comprises a spacer flange 434 that includes a first planar mounting surface 436 for permanently mounting the sensor mount 432 to the C-arm 125, and a second planar mounting surface 438 from which a handle 440 extends. The handle 440 forms an aperture 441 between it and the second planar surface 438 for receiving the clip 414 of the sensor housing 406 in a direction parallel to the first planar mounting surface 436. In the illustrated embodiment, the aperture 441 exhibits a cross-section substantially dissimilar to that of the clip 414, and in this case a semi-circular cross-section, so that the handle 440 snugly holds the clip 414. The length of the spacer flange 434 is substantially shorter than that of the clip 414.

Specifically referring to FIG. 7F, a sensor mount 442 comprises a spacer flange 444 that includes a first planar mounting surface 446 for permanently mounting the sensor mount 442 to the C-arm 125, and a second planar mounting surface 448 from which a handle 450 extends. The handle 450 forms an aperture 452 between it and the second planar surface 448 for receiving the clip 414 of the sensor housing 406 in a direction parallel to the first planar mounting surface 446. In the illustrated embodiment, the aperture 452 exhibits a cross-section substantially dissimilar to that of the clip 414, and in this case a rectangular cross-section, so that the handle 450 snugly holds the clip 414. The length of the spacer flange 444 is substantially the same as that of the clip 414. To further ensure a tight fit between the sensor housing 406 and the sensor mount 442, a pair of sensor receiving arms 454 extend from the second planar surface 448 of the spacer flange 442. The pair of arms 454 includes ends 456, which curve towards each other to define an aperture 458 having a cross-section that substantially matches that of the shaft 408 of the sensor housing 406, thereby allowing the arms 454 to grip the shaft 408 of the mounted sensor housing 406.

FIG. 7G depicts an alternative embodiment of sensor mount 462 that is similar to the afore-described sensor mount 402, with the exception that the means for receiving the clip 414 comprises a slit that is formed in the spacer flange. Specifically, the sensor mount 462 comprises a spacer flange 464 that includes a planar mounting surface 466 for permanently mounting the sensor mount 462 to the C-arm 125. The sensor mount 462 further includes an elastomer slit 468 formed within the spacer flange 464 to receive the clip 414 of the sensor housing 406 in a direction parallel to the planar mounting surface 466. Preferably, the size of the slit 468 is slightly smaller than the size of the clip 414, such that the slit 414 expands in a gripping relationship with the inserted clip 414 to snugly engage the sensor 404 with the sensor mount 462.

FIG. 7H depicts an alternative embodiment of sensor mount 472 that is similar to the afore-described sensor mount 402, with the exception that the means for receiving the clip 414 comprises an L-shaped flange that extends from the spacer flange. Specifically, the sensor mount 472 comprises a spacer flange 474 that includes a first planar mounting surface 476 for permanently mounting the sensor mount 472 to the C-arm 125, and a second planar mounting surface 478 from which an L-shaped flange 480 extends. The L-shaped flange 480 forms an open slot 481 between it and the second planar surface 478 for receiving the clip 414 of the sensor housing 406 in a direction parallel to the first planar mounting surface 476.

FIG. 7I depicts an alternative embodiment of sensor mount 482 that is similar to the afore-described sensor mount 402, with the exception that the means for receiving the clip 414 comprises a spring clip that extends from the spacer flange. Specifically, the sensor mount 482 comprises a spacer flange 484 that includes a first planar mounting surface 486 for permanently mounting the sensor mount 482 to the C-arm 125, and a second planar mounting surface 488 from which a spring clip 490 extends. The spring clip 490 forms an open slot 494 between it and the second planar surface 488 for receiving the shaft 408 of the sensor housing 406 in a direction parallel to the first planar mounting surface 486. The spring action of the clip 490 compresses the mounted sensor 404 against the spacer flange 484 in a snug relationship. The spring clip 490 also includes a cutout 494 that receives and accommodates the shaft 408 of the sensor housing 406 when the sensor 404 is mounted.

Figure 8A:
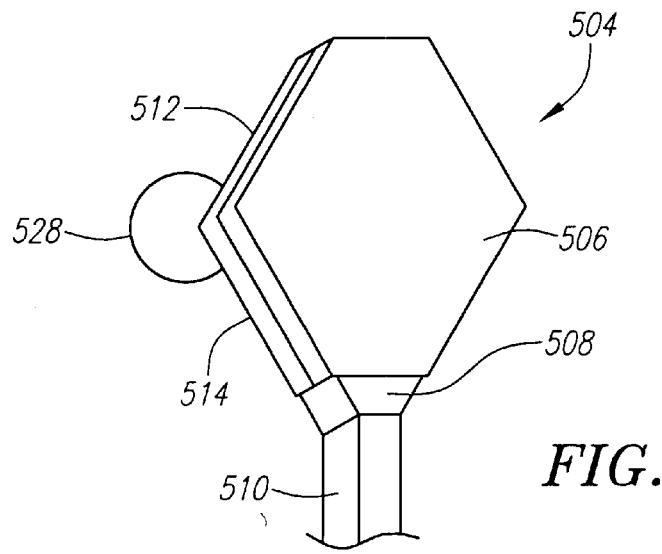
FIG. 8A depicts a perspective view of a sensor.
Figure 8B:
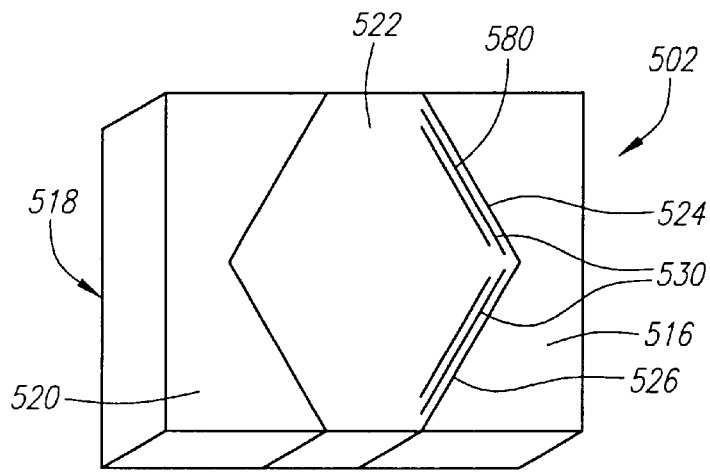
FIG. 8B depicts a perspective view of a sensor mount for use with the sensor of FIG. 8A.
Figure 8C:
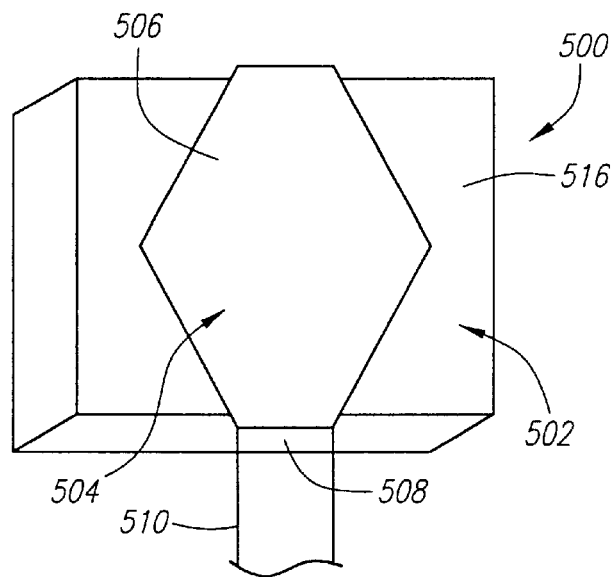
FIG. 8C depicts a perspective view of the sensor of FIG. 8A mounted in the sensor mount of FIG. 8B.

Referring now to FIGS. 8A–8C, still another preferred embodiment of a sensor assembly 500 is depicted. The sensor assembly 500 comprises a sensor mount 502 (shown separately in FIG. 8B) and a sensor 554 (shown separately in FIG. 8A), which is removably attached to the sensor mount 502. The sensor 504 comprises a sensor housing 506, which contains sensing elements (not depicted) and an outlet 508 at one end from which sensor wires 510 extend. The sensor housing 506 may be of any shape, e.g., hexagonal, that has at least two lateral edges 512 and 514. In fact, any shape other than a circle is contemplated to prevent rotation of the sensor housing 506 when mounted in the sensor mount 502.

The sensor mount 502 comprises a planar spacer flange 516, which spaces the mounted sensor 504 the required distance away from the C-arm 125. To this end, the spacer flange 516 comprises a first planar mounting surface 518, which is the surface used to permanently attach the sensor mount 502 to the C-arm 125 via suitable means, such as welding or bonding, and an oppositely-disposed second planar mounting surface 520 in which an open cavity 522 is formed for receiving the sensor housing 506 in a direction perpendicular to the first planar mounting surface 520. The shape and size of the sensor housing 506 and open cavity 522 are substantially the same, such that the sensor housing 506 is snugly disposed within the open cavity 522 in a snap-fit arrangement. Thus, the open cavity 522 is defined by at least two lateral edges 524 and 526 that engage the at least two lateral edges 512 and 514 of the sensor housing 506 when the sensor 504 is mounted in the open cavity 522. To further enhance the secure fit between the sensor mount 502 and the sensor 504, the lateral edges 512 and 514 of the sensor 504 preferably each include at least one ridge 528, and the lateral edges 524 and 526 of the open cavity 522 each include at least one mating indentation 530. Alternatively, the lateral edges 512 and 514 of the sensor 504 include at least one indentation, and the lateral edges 524 and 526 of the open cavity 522 each include at least one mating ridge.

Referring now to FIGS. 9A–9D, still another preferred embodiment of a sensor assembly 550 is depicted. As illustrated in FIG. 9D, the sensor assembly 550 comprises a sensor mount 552 and a sensor 554. Referring specifically to FIG. 9A, the sensor 554 comprises a sensor housing 556, which contains sensing elements (not depicted). The sensor housing 556 has a substantially tubular shaft 558 that includes an outlet 560 at one end from which sensor wires 562 extend. Referring specifically to FIG. 9B, the sensor mount 552 comprises a planar spacer flange 564, which spaces the mounted sensor 554 the required distance away from the C-arm 125. The spacer flange 564 comprises a circular cavity 566 in which the sensor 554 is mounted, e.g., by bonding, with the tubular shaft 558 being disposed along the diameter of the circular cavity 566, and the opposite ends thereof being in contact with a wall 568 of the cavity 566. The spacer flange 564 further comprises a planar mounting surface 570, which as will be described below, is the surface used to removably attach the spacer flange 564 to a patch 572 of the sensor mount 552.

Referring specifically to FIG. 9C, the patch 572 comprises a first planar mounting surface 574, which is the surface used to permanently attach the sensor mount 552 to the C-arm 125 via suitable means, such as welding or bonding, and an oppositely-disposed second planar mounting surface 576, which is configured, such that the spacer flange 564 can be removably mounted thereto, as illustrated in FIG. 9D. In the illustrated embodiment, a hook-in-loop material 578, the hook portion of which is permanently disposed on the planar surface 570 of the spacer flange 564, and the loop portion of which is permanently disposed on the second planar surface 576 of the patch 572, is used to removably mount the spacer flange 564 to the patch 572.

Figure 10A:
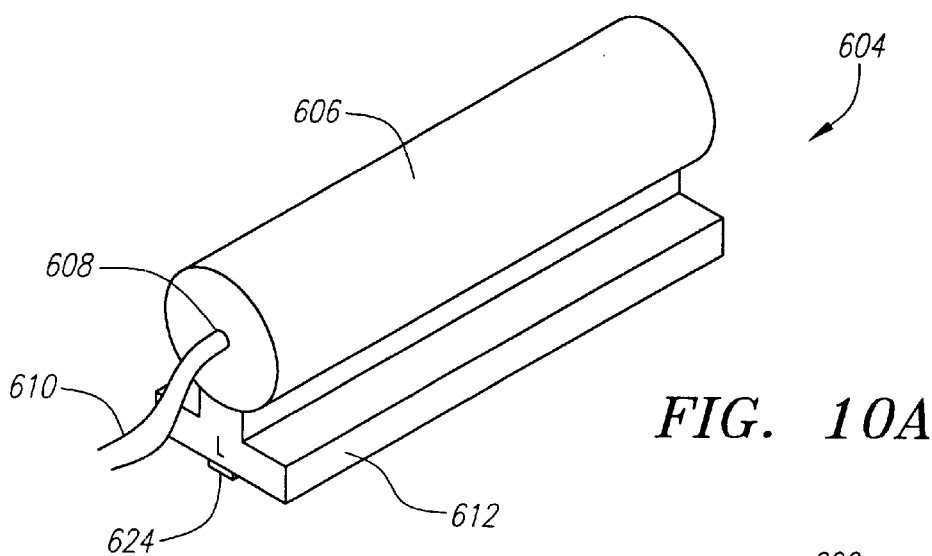
FIG. 10A depicts a perspective view of a sensor.
Figure 10B:
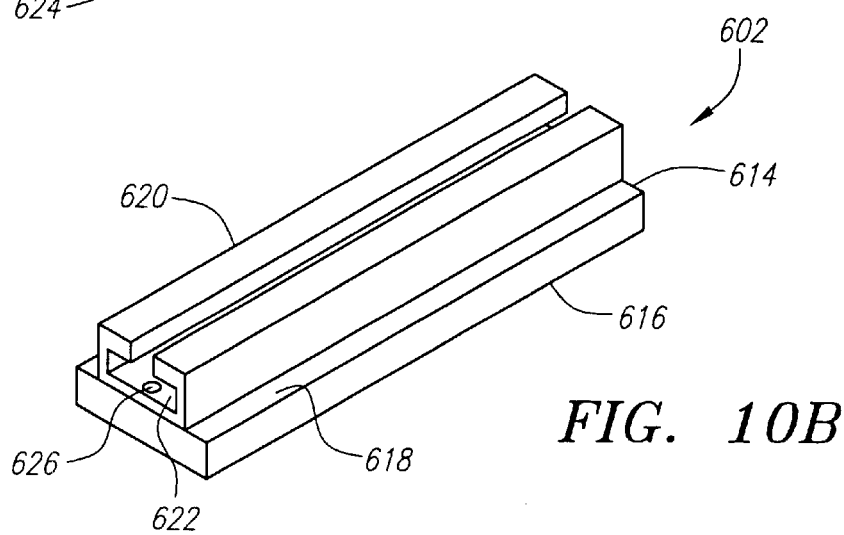
FIG. 10B depicts a perspective view of a sensor mount for use with the sensor of FIG. 10A.
Figure 10C:
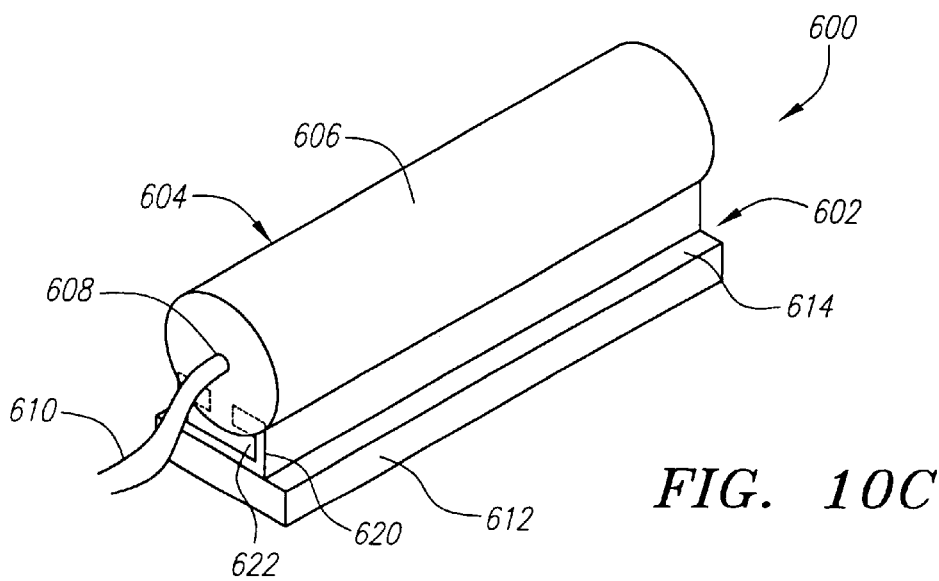
FIG. 10C depicts a perspective view of the sensor of FIG. 10A mounted in the sensor mount of FIG. 10B.

Referring now to FIGS. 10A–10C, still another preferred embodiment of a sensor assembly 600 is depicted. The sensor assembly 600 comprises a sensor mount 602 (shown separately in FIG. 10B) and a sensor 604 (shown separately in FIG. 10A), which is removably attached to the sensor mount 602. The sensor 604 comprises a cylindrical sensor housing 606, which contains sensing elements (not depicted) and an outlet 608 at one end, from which sensor wires 610 extend. The sensor 604 further includes a member 612 that extends the length of the sensor housing 606.

The sensor mount 602 comprises a planar spacer flange 614, which spaces the mounted sensor 604 the required distance away from the C-arm 125. To this end, the spacer flange 614 comprises a first planar mounting surface 616, which is the surface used to permanently attach the sensor mount 602 to the C-arm 125 via suitable means, such as welding or bonding, and an oppositely-disposed second planar mounting surface 618, from which a member 620 extends. A cavity 622 is formed in the member 620, and extends the length of the spacer flange 614.

The member 612 of the sensor 604 and the cavity 622 of the sensor mount 602 have substantially uniform and complementary cross-sections, and in this case T-shaped cross-sections, such that they are configured to slidingly engage each other in a direction parallel to the first planar mounting surface 616 of the sensor mount 602. To further ensure a secure fit between the sensor 604 and the sensor mount 602, the T-shaped member 612 includes a protuberance 624, and the T-shaped cavity 622 comprises an indentation 626 that engage each other in a snap-fit arrangement when the T-shaped member 612 is fully engaged with the T-shaped cavity 622, as illustrated in FIG. 10C.

Referring now to FIGS. 11A1–11C, still another preferred embodiment of a sensor assembly 650 is depicted. The sensor assembly 650 is similar to the previously described sensor assembly 600, with the exception that a trapezoidal-shaped member and cavity arrangement is used. Specifically, the sensor assembly 650 comprises a sensor mount 652 (shown separately in FIG. 11B) and a sensor 654 (shown separately in FIG. 11A), which is removably attached to the sensor mount 652. The sensor 654 comprises a sensor housing 656, which contains sensing elements (not depicted) and an outlet 658 at one end from which sensor wires 660 extend. The sensor 654 further includes a member 662 that extends the length of the sensor housing 656.

The sensor mount 652 comprises a planar spacer flange 664, which spaces the mounted sensor 654 the required distance away from the C-arm 125. To this end, the spacer flange 664 comprises a planar mounting surface 666, which is the surface used to permanently attach the sensor mount 652 to the C-arm 125 via suitable means, such as welding or bonding. The spacer flange 664 further comprises a cavity 668 formed therein that extends the length of the sensor housing 656.

The member 662 of the sensor 654 and the cavity 668 of the sensor mount 652 have substantially uniform and complementary cross-sections, and in this case, trapezoidal-shaped cross-sections, such that they are configured to slidingly engage each other in a direction parallel to the planar mounting surface 666 of the sensor mount 652. To further ensure a secure fit between the sensor 654 and the sensor mount 652, the trapezoidal-shaped member 662 includes a protuberance 670, and the trapezoidal-shaped cavity 668 comprises an indentation 672 that engage each other in a snap-fit arrangement when the trapezoidal-shaped member 662 is fully engaged with the trapezoidal-shaped cavity 672, as illustrated in FIG. 11C. The sensor 654 conveniently includes a finger handle 674, which can be grasped by the user to slide the member 662 of the sensor 654 into and out of the cavity 668 of the sensor mount 652.

Figure 12A:
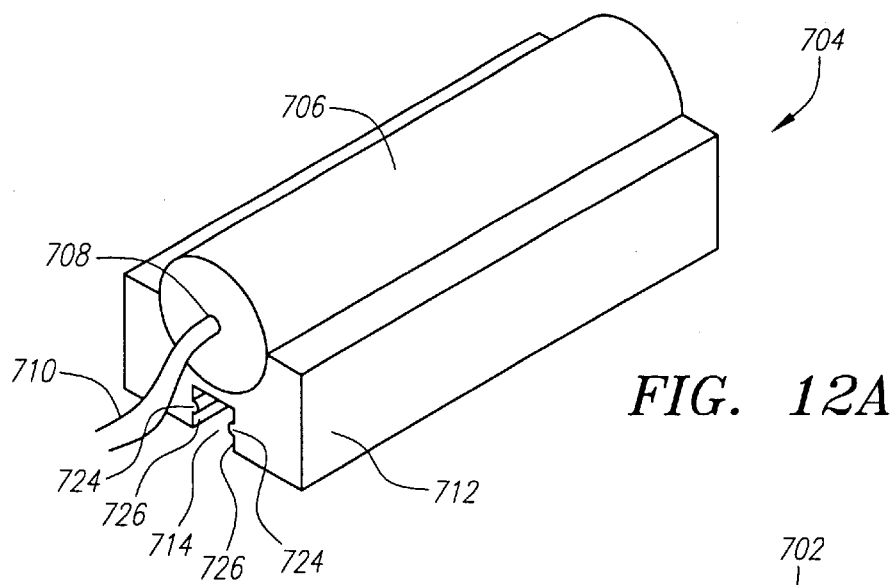
FIG. 12A depicts a perspective view of a sensor.
Figure 12B:
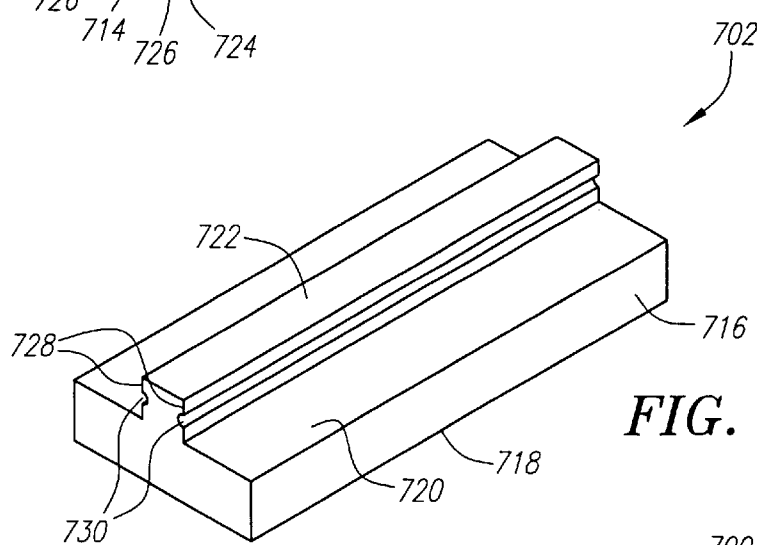
FIG. 12B depicts a perspective view of a sensor mount for use with the sensor of FIG. 12A.
Figure 12C:
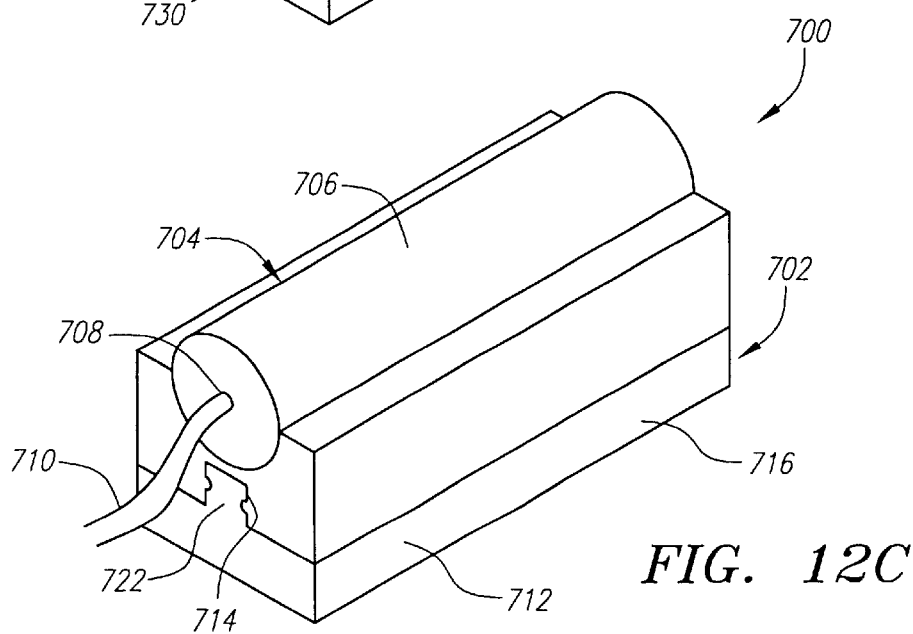
FIG. 12C depicts a perspective view of the sensor of FIG. 12A mounted in the sensor mount of FIG. 12B.

Referring now to FIGS. 12A–12C, still another preferred embodiment of a sensor assembly 700 is depicted. The sensor assembly 700 comprises a sensor mount 702 (shown separately in FIG. 12B) and a sensor 704 (shown separately in FIG. 11A), which is removably attached to the sensor mount 702. The sensor 704 comprises a sensor housing 706, which contains sensing elements (not depicted) and an outlet 708 at one end from which sensor wires 710 extend. The sensor 704 further includes a member 712 that forms a cavity 714 that extends the length of the sensor housing 706.

The sensor mount 702 comprises a planar spacer flange 716, which spaces the mounted sensor 704 the required distance away from the C-arm 125. To this end, the spacer flange 716 comprises a first planar mounting surface 718, which is the surface used to permanently attach the sensor mount 702 to the C-arm 125 via suitable means, such as welding or bonding, and an oppositely-disposed second planar mounting surface 720 from which a member 722 extends along the length of the spacer flange 716.

The cavity 714 of the sensor 704 and the member 722 of the sensor mount 702 have substantially uniform and complementary cross-sections, and in this case, rectangular-shaped cross-sections, such that they are configured to slidingly engage each other in a direction parallel to the first planar mounting surface 718 of the sensor mount 702. To further ensure a secure fit between the sensor 704 and the sensor mount 702, the rectangular-shaped cavity 714 includes opposing sidewalls 724, each with a ridge 726 that extends the length thereof, and the rectangular-shaped member 722 includes opposing sidewalls 728, each with a slot 730 that extends the length thereof. The ridges 726 and slots 730 engage each other in a friction fit, as the rectangular member 722 is engaged with the rectangular cavity 714, as illustrated in FIG. 12C.

Figure 13A:
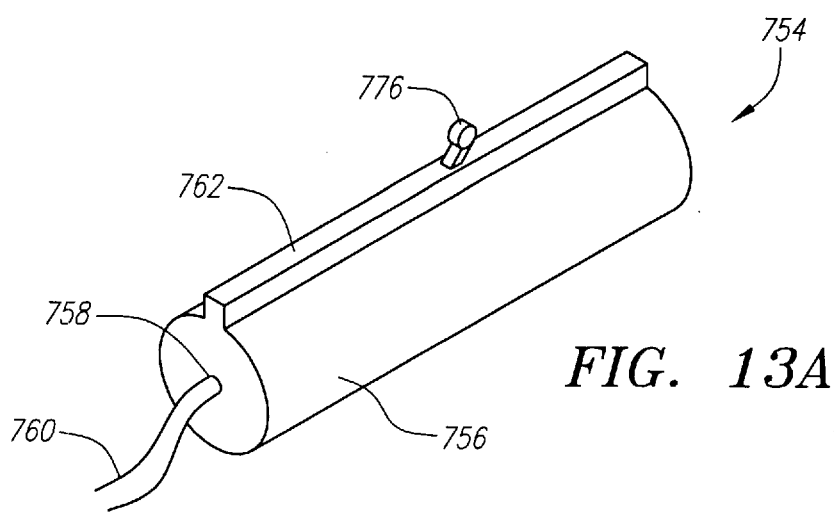
FIG. 13A depicts a perspective view of a sensor.
Figure 13B:
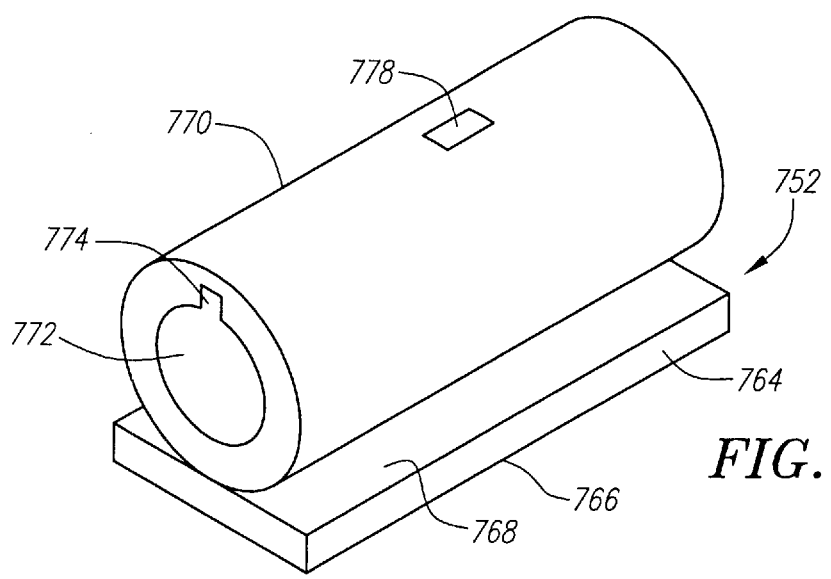
FIG. 13B depicts a perspective view of a sensor mount for use with the sensor of FIG. 13A.
Figure 13C:
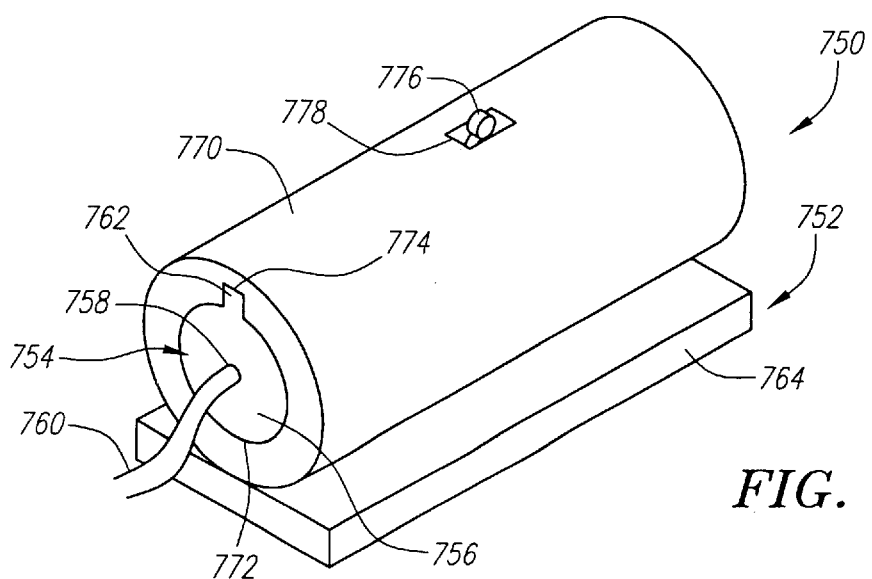
FIG. 13C depicts a perspective view of the sensor of FIG. 13A mounted in the sensor mount of FIG. 13B.

Referring now to FIGS. 13A–13C, still another preferred embodiment of a sensor assembly 750 is depicted. The sensor assembly 750 comprises a sensor mount 752 (shown separately in FIG. 13B) and a sensor 754 (shown separately in FIG. 13A), which is removably attached to the sensor mount 752. The sensor 754 comprises a cylindrical sensor housing 756, which contains sensing elements (not depicted) and an outlet 758 at one end, from which sensor wires 760 extend. For purposes that will be described below, the sensor housing 756 further includes a key 762 that extends along the length thereof.

The sensor mount 752 comprises a planar spacer flange 764, which spaces the mounted sensor 754 the required distance away from the C-arm 125. To this end, the spacer flange 764 comprises a first planar mounting surface 766, which is the surface used to permanently attach the sensor mount 752 to the C-arm 125 via suitable means, such as welding or bonding, and an oppositely-disposed second planar mounting surface 768, from which a member 770 extends. The member 770 comprises a cylindrical cavity 772 formed therein that extends along the length of the spacer flange 764. The cylindrical cavity 772 comprises a key slot 774 that extends along the length thereof.

The sensor housing 756 and the cavity 772 of the sensor mount 752 have substantially uniform and complementary cross-sections, and in this case, elliposidal-shaped cross-sections, and specifically circular-shaped cross-sections, such that they are configured to slidingly engage each other in a direction parallel to the first planar mounting surface 766 of the sensor mount 752. Additionally, the key 762 of the sensor housing 756 fits in and engages with the key slot 774 of the cylindrical cavity 772, such that the cylindrical sensor housing 756 does not rotate along the axis of the cylindrical cavity 772. To further ensure a secure fit between the sensor 754 and the sensor mount 752, the cylindrical sensor housing 756 includes a detent 776, and the cylindrical cavity 772 includes an aperture 778 that engage each other when the cylindrical sensor housing 756 is fully engaged with the cylindrical cavity 772, as illustrated in FIG. 13C.

Figure 14A:
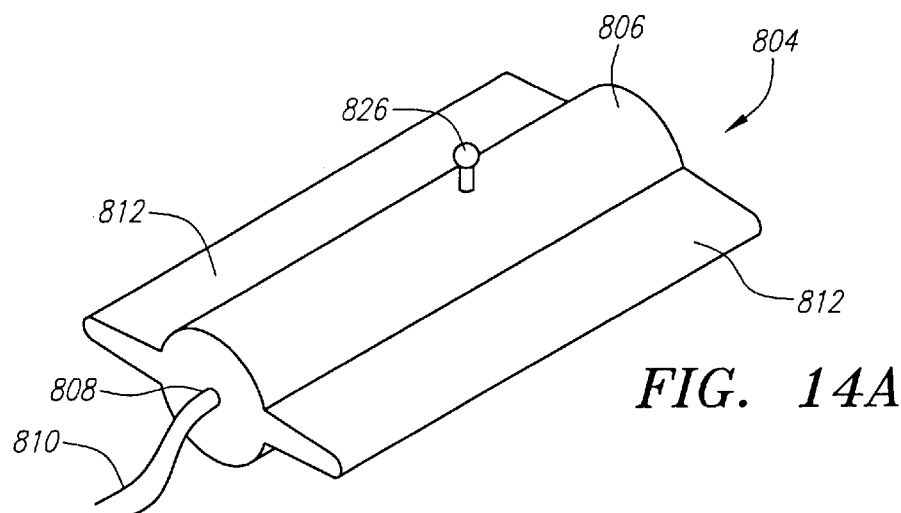
FIG. 14A depicts a perspective view of a sensor.
Figure 14B:
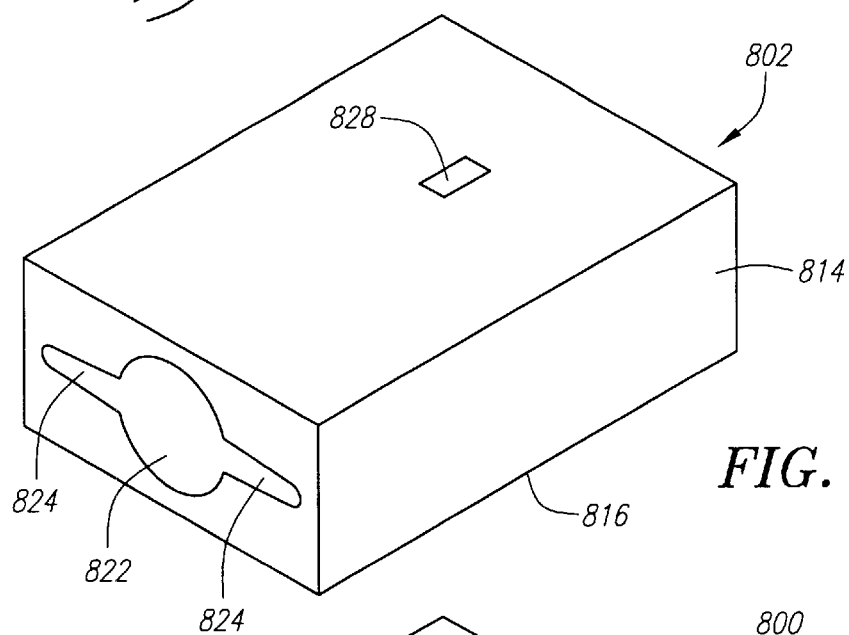
FIG. 14B depicts a perspective view of a sensor mount for use with the sensor of FIG. 14A.
Figure 14C:
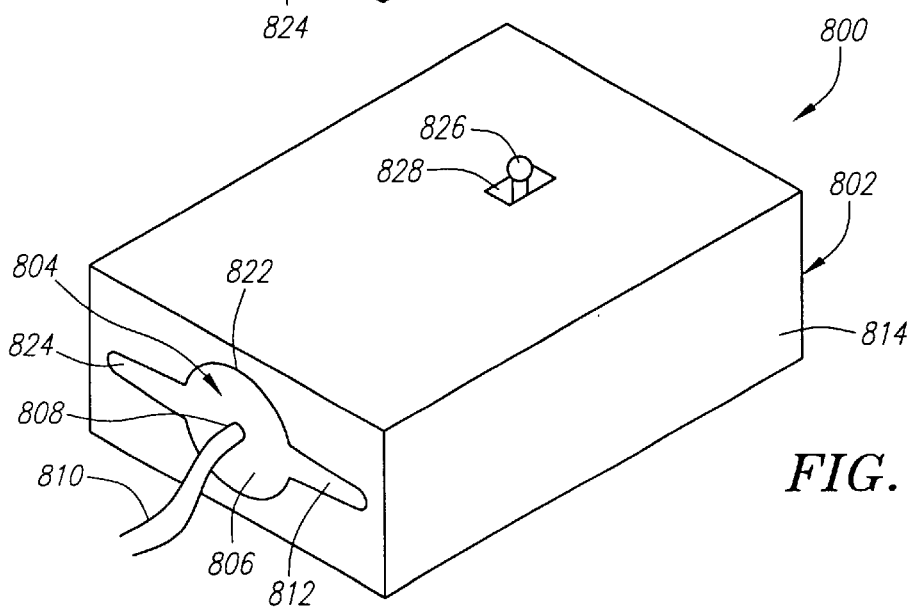
FIG. 14C depicts a perspective view of the sensor of FIG. 14A mounted in the sensor mount of FIG. 14B.

Referring now to FIGS. 14A-14C, still another preferred embodiment of a sensor assembly 800 is depicted. The sensor assembly 800 is similar to the previously described sensor assembly 750, with the exception that opposing extensions, rather than a key, is used to prevent rotation of the sensor housing. Specifically, the sensor assembly 800 comprises a sensor mount 802 (shown separately in FIG. 14B) and a sensor 804 (shown separately in FIG. 14A), which is removably attached to the sensor mount 802. The sensor 804 comprises a generally cylindrical sensor housing 806, which contains sensing elements (not depicted) and an outlet 808 at one end, from which sensor wires 810 extend. For purposes that will be described below, the sensor housing 806 further includes a pair of lateral opposing extensions 812.

The sensor mount 802 comprises a spacer flange 814, which spaces the mounted sensor 804 the required distance away from the C-arm 125. To this end, the spacer flange 814 comprises a planar mounting surface 816, which is the surface used to permanently attach the sensor mount 802 to the C-arm 125 via suitable means, such as welding or bonding. The sensor mount 802 further comprises a cylindrical cavity 822 that is formed within the spacer flange 814 extends along the length of the spacer flange 814. The cylindrical cavity 822 comprises a pair of lateral opposing extensions 824 that extends along the length thereof.

The sensor housing 806 and the cavity 822 of the sensor mount 802 have substantially uniform and complementary cross-sections, and in this case, elliposidal-shaped cross-sections, and specifically circular-shaped cross-sections, such that they are configured to slidingly engage each other in a direction parallel to the planar mounting surface 816 of the sensor mount 802. Additionally, the pair of opposing lateral extensions 812 of the sensor housing 806 fits in and engages with the pair of opposing lateral extensions 824 of the cylindrical cavity 822, such that the cylindrical sensor housing 806 does not rotate along the axis of the cylindrical cavity 822. To further ensure a secure fit between the sensor 804 and the sensor mount 802, the cylindrical sensor housing 806 includes a detent 826, and the cylindrical cavity 822 includes an aperture 828 that engage each other when the cylindrical sensor housing 806 is fully engaged with the cylindrical cavity 822, as illustrated in FIG. 14C.

Figure 15A:
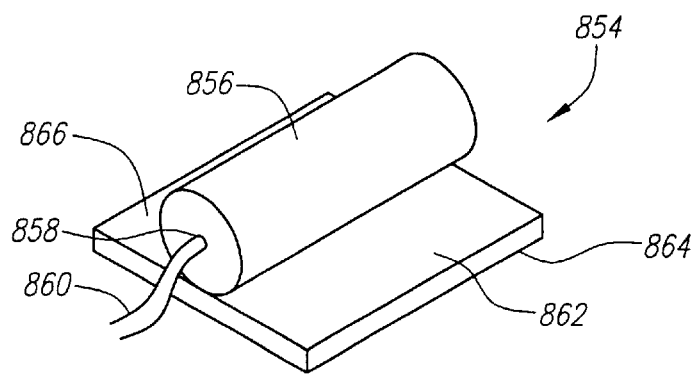
FIG. 15A depicts a perspective view of a sensor.
Figure 15B:
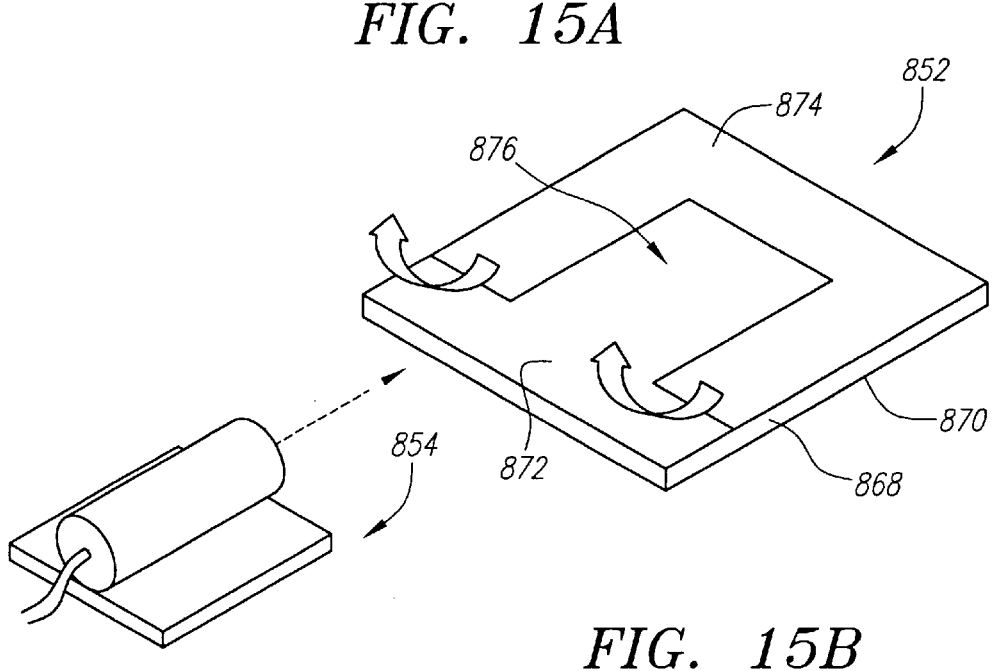
FIG. 15B depicts a perspective view of a sensor mount for use with the sensor of FIG. 15A.
Figure 15C:
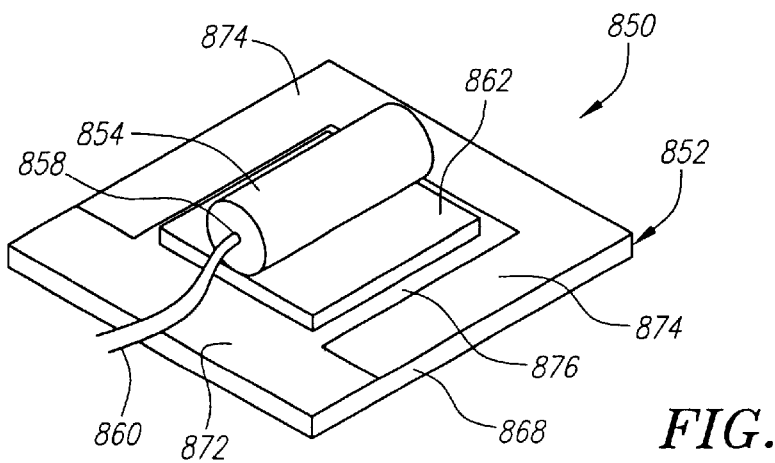
FIG. 15C depicts a perspective view of the sensor of FIG. 15A mounted in the sensor mount of FIG. 15B.

Referring now to FIGS. 15A–15C, still another preferred embodiment of a sensor assembly 850 is depicted. The sensor assembly 850 comprises a sensor mount 852 (shown separately in FIG. 15B) and a sensor 854 (shown separately in FIG. 15A), which is removably attached to the sensor mount 852. The sensor 854 comprises a cylindrical sensor housing 856, which contains sensing elements (not depicted) and an outlet 858 at one end, from which sensor wires 860 extend. The sensor 854 further includes a rigid planar member 862, which includes a first planar surface 864 and an oppositely-disposed second planar surface 866, from which the sensor housing 856 extends.

The sensor mount 852 comprises a planar spacer flange 868, which spaces the mounted sensor 854 the required distance away from the C-arm 125. To this end, the spacer flange 868 comprises a first planar mounting surface 870, which is the surface used to permanently attach the sensor mount 852 to the C-arm 125 via suitable means, such as welding or bonding, and an oppositely-disposed second planar mounting surface 872. The sensor mount 852 further includes a flexible planar member 874 that is configured to be removably attached to the second planar mounting surface 872 of the spacer flange 868. The flexible planar member 874 comprises an aperture 876, through which the sensor housing 856 can fit through, but through which the rigid planar member 862 cannot.

Thus, the spacer flange 868, with the sensor housing 856, can be inserted between the flexible planar member 874 and the spacer flange 868 when removably attaching the flexible planar member 874 to the spacer flange 868, thereby removably mounting the sensor 854 to the sensor mount 852, as illustrated in FIG. 15C. In the illustrated embodiment, a hook-in-loop material (not illustrated), the hook portion of which forms the flexible planar member 874, and the loop portion of which is permanently disposed on the second planar surface 872 of the spacer flange 868, is used to removably mount the rigid planar member 862, and thus, the sensor 854, to the sensor mount 852.

Figure 16A:
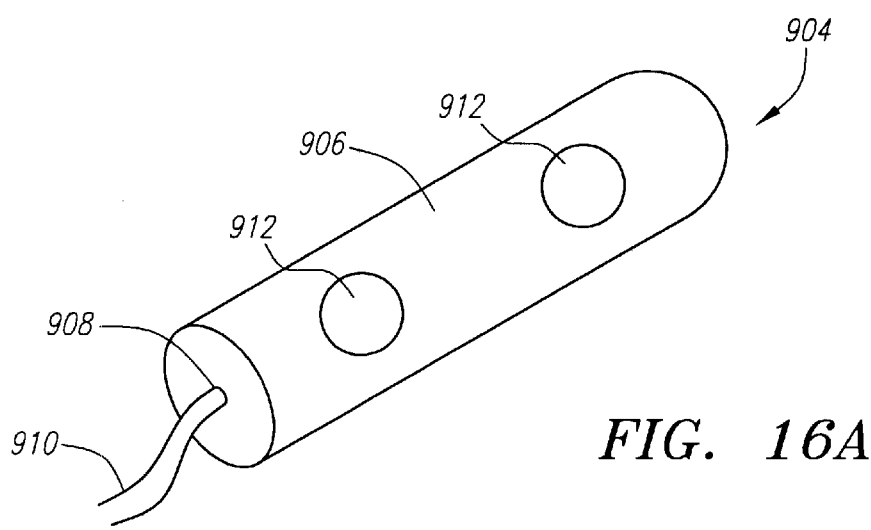
FIG. 16A depicts a perspective view of a sensor.
Figure 16B:
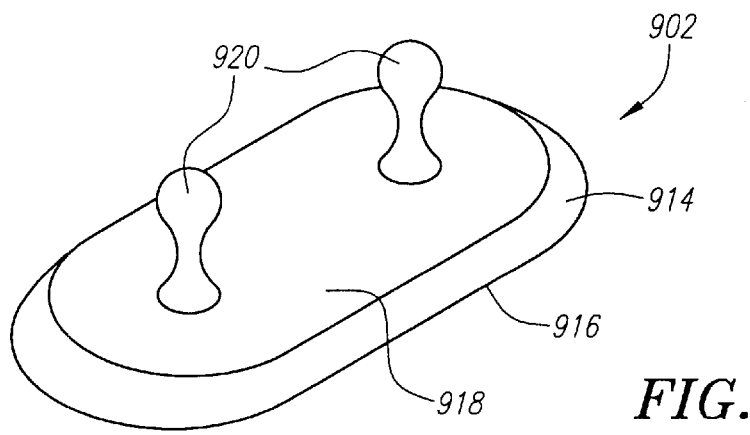
FIG. 16B depicts a perspective view of a sensor mount.
Figure 16C:
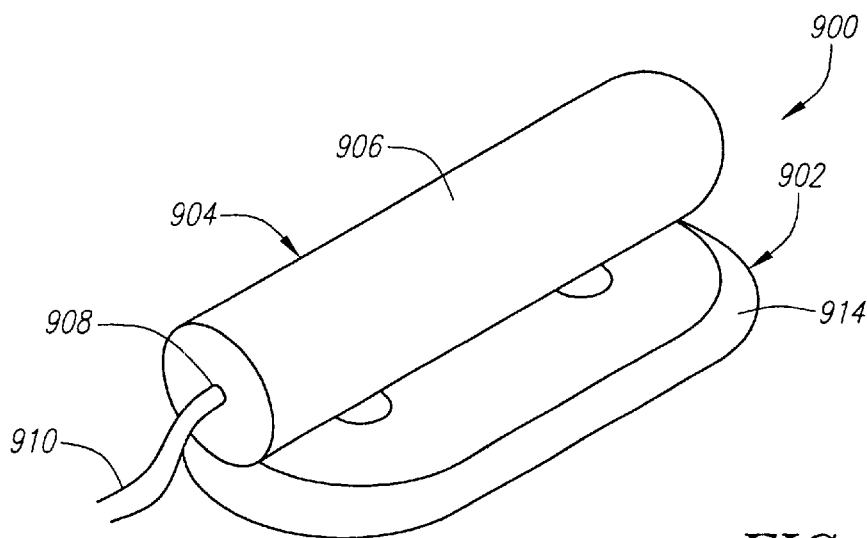
FIG. 16C depicts a perspective view of the sensor of FIG. 16A mounted in the sensor mount of FIG. 16B.

Referring now to FIGS. 16A–16C, still another preferred embodiment of a sensor assembly 900 is depicted. The sensor assembly 900 comprises a sensor mount 902 (shown separately in FIG. 16B) and a sensor 904 (shown separately in FIG. 16A), which is removably attached to the sensor mount 902. The sensor 904 comprises a cylindrical sensor housing 906, which contains sensing elements (not depicted) and an outlet 908 at one end, from which sensor wires 910 extend. The sensor 904 further includes a pair of axially aligned snap holes 912 that is formed within the sensor housing 906.

The sensor mount 902 comprises a planar spacer flange 914, which spaces the mounted sensor 904 the required distance away from the C-arm 125. To this end, the spacer flange 914 comprises a first planar mounting surface 916, which is the surface used to permanently attach the sensor mount 902 to the C-arm 125 via suitable means, such as welding or bonding, and an oppositely-disposed second planar mounting surface 918, from which a pair of axially aligned snap protuberances 920 extend. The spacing between, and size of, the pair of snap holes 912 and the spacing between, and size of, the pair of snap protuberances 920 match, such that they are configured to snap together to mount the sensor 904 on the sensor mount 902, as illustrated in FIG. 16C.

Figure 17A:
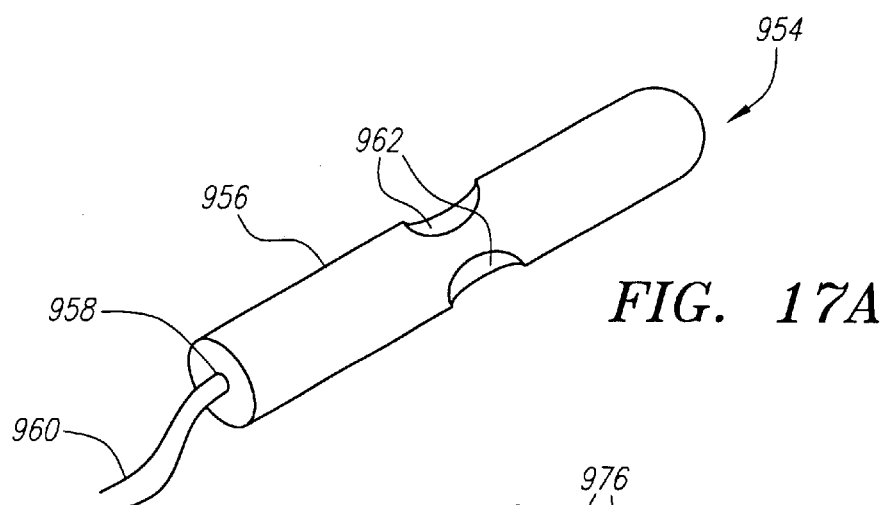
FIG. 17A depicts a perspective view of a sensor.
Figure 17B:
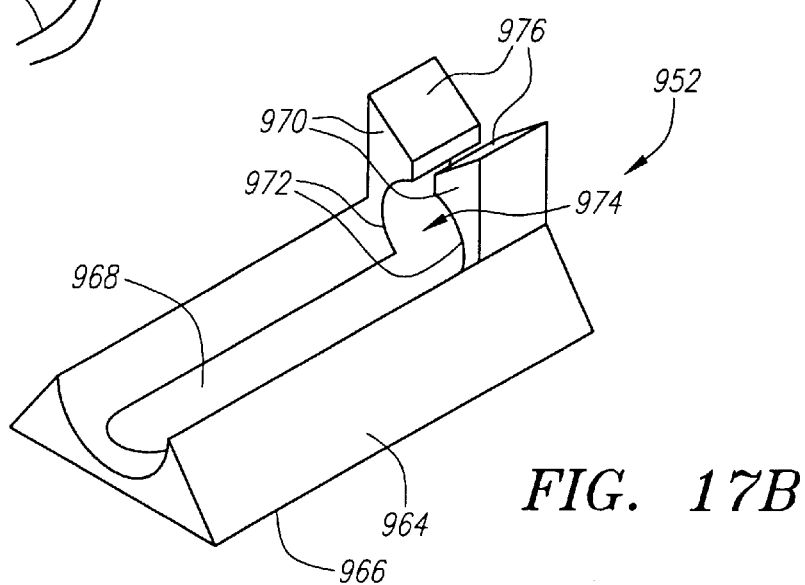
FIG. 17B depicts a perspective view of a sensor mount for use with the sensor of FIG. 17A.
Figure 17C:
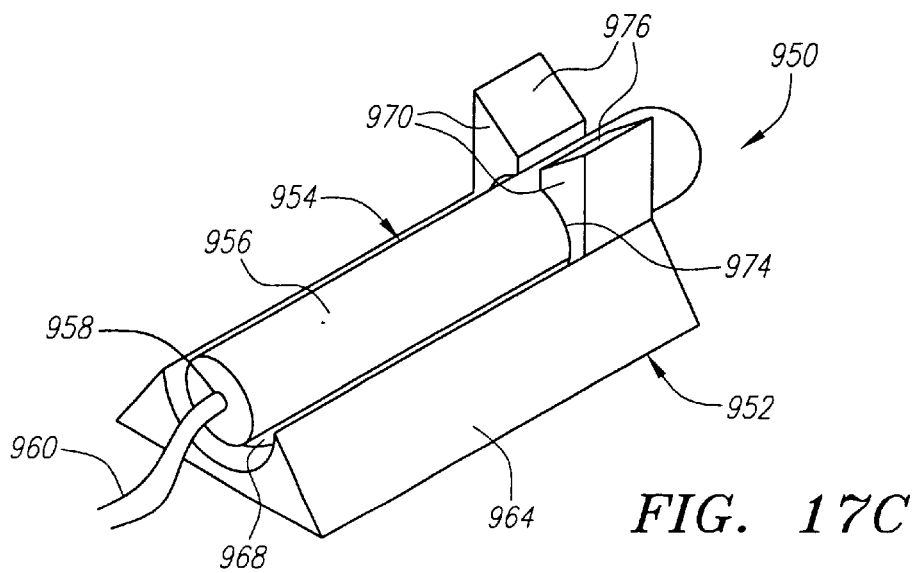
FIG. 17C depicts a perspective view of the sensor of FIG. 17A mounted in the sensor mount of FIG. 17B.

Referring now to FIGS. 17A–17C, still another preferred embodiment of a sensor assembly 950 is depicted. The sensor assembly 950 comprises a sensor mount 952 (shown separately in FIG. 17B) and a sensor 954 (shown separately in FIG. 17A), which is removably attached to the sensor mount 952. The sensor 954 comprises a cylindrical sensor housing 956, which contains sensing elements (not depicted) and an outlet 958 at one end, from which sensor wires 960 extend. The sensor housing 956 includes two oppositely-disposed cutouts 962, which are preferably provided at or near the midpoint of the sensor housing 956.

The sensor mount 952 comprises a spacer flange 964, which spaces the mounted sensor 954 the required distance away from the C-arm 125. To this end, the spacer flange 964 comprises a planar mounting surface 966, which is the surface used to permanently attach the sensor mount 952 to the C-arm 125 via suitable means, such as welding or bonding, and an oppositely-disposed concave surface 968 that is sized and shaped to receive the sensor housing 956. A pair of sensor holding arms 970 extends from the concave surface 968 of the spacer flange 964, and includes opposing concave surfaces 972 that define an aperture 974 between the arms 970. The holding arms 970 are configured to grip the sensor housing 956 therebetween in a snap-fit arrangement when the concave surfaces 972 are coincident with the cutouts 962 of the sensor housing 956, as illustrated in FIG. 17C. The concave surface 968 of the spacer flange 964 receives the sensor housing 956, thereby further ensuring a secure fit between the sensor 954 and the sensor mount 952. Each of the pair of sensor arms 970 comprises a beveled edge 976, which guides and facilitates the insertion of the sensor housing 956 between the arms 970 and into the aperture 974. Preferably, the sensor holding arms 970 are composed of a resilient material having an elastic property, such as an elastomer, so that their shape may be distorted as the sensor housing 956 is inserted therebetween, yet at least partially restored once inserted.

Figure 18A:
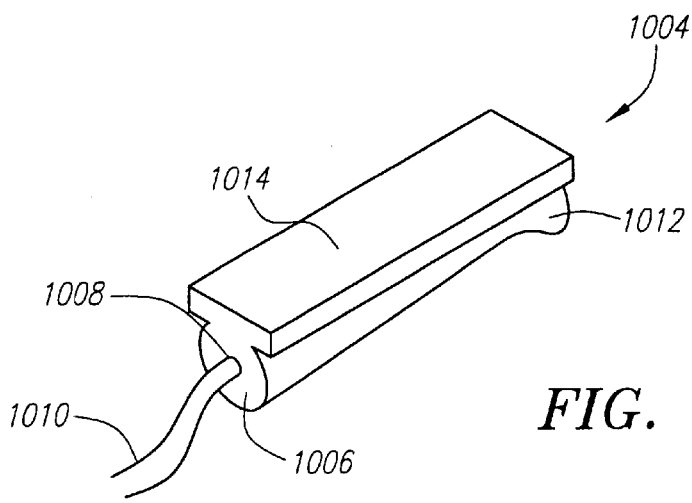
FIG. 18A depicts a perspective view of a sensor.
Figure 18B:
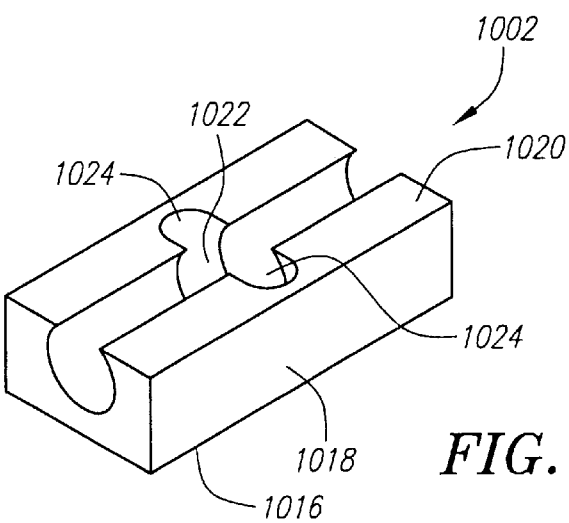
FIG. 18B depicts a perspective view of a sensor mount for use with the sensor of FIG. 18A.
Figure 18C:
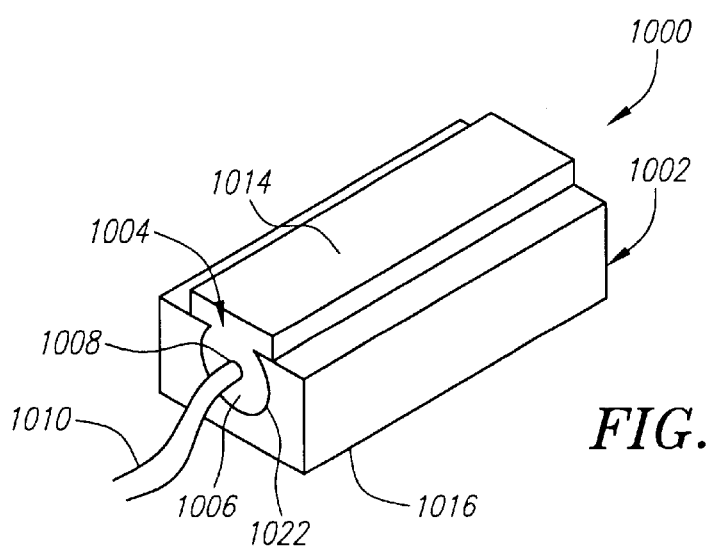
FIG. 18C depicts a perspective view of the sensor of FIG. 18A mounted in the sensor mount of FIG. 18B.

Referring to FIGS. 18A–18C, still another preferred embodiment of a sensor assembly 1000 is depicted. The sensor assembly 1000 comprises a sensor mount 1002 (shown separately in FIG. 18B) and a sensor 1004 (shown separately in FIG. 18A), which is removably attached to the sensor mount 1002. The sensor 1004 comprises a generally cylindrical sensor housing 1006, which contains sensing elements (not depicted). For purposes that will be described in further detail below, the cross-section of the cylindrical sensor housing 1006 forms a semi-circle that exhibits an arc of greater than 180 degrees. The sensor housing 1006 has an outlet 1008 at one end, from which sensor wires 1010 extend. The sensor housing 1006 further comprises extensions 1012 that extend perpendicularly from the sensor housing 1006 in opposite directions. The sensor 1004 further includes a planar flange 1014 that has a planar surface 1016, from which the sensor housing 1006 extends.

The sensor mount 1002 comprises a planar spacer flange 1016, which spaces the mounted sensor 1004 the required distance away from the C-arm 125. To this end, the spacer flange 1004 comprises a first planar mounting surface 1018, which is the surface used to permanently attach the sensor mount 1002 to the C-arm 125 via suitable means, such as welding or bonding, and an oppositely-disposed second planar mounting surface 1020, in which a generally cylindrical open cavity 1022 is formed for receiving the sensor housing 1006. The cross-section of the generally cylindrical cavity 1022 forms a semi-circle that exhibits an arc of greater than 180 degrees, such that it receives the generally cylindrical housing 1006 in a snap-fit arrangement, as illustrated in FIG. 18C. The coincidence between the planar surface 1016 of the sensor 1004 and the second planar mounting surface 1020 of the spacer flange 1016 prevents the sensor housing 1006 from rotating relative to the axis of the cavity 1022. Additionally, the cavity 1022 further comprises extensions 1024 that extend perpendicularly therefrom, in opposite directions, to receive the lateral extensions 1012 of the sensor housing 1006, thereby ensuring that the sensor housing 1006 does not rotate within the cavity 1022.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims. All publications, patents, and patent applications cited herein are hereby incorporated by reference in their entirety for all purposes.

What is claimed is:

1. A medical sensor assembly for use with a fluoroscopic mount, comprising:
   an electromagnetic sensor configured for outputting positional data relating to said fluoroscopic mount, said sensor comprising a mount engaging element; and
   a sensor mount composed of a non-ferromagnetic material, said sensor mount comprising a spacer and a sensor engaging element, wherein said sensor engaging element and said mount engaging element are configured to be removably mounted in an interference relationship with each other, and said spacer is configured to maintain a prescribed distance between said sensor and said fluoroscopic mount.

2. The medical sensor assembly of claim 1, wherein said fluoroscopic mount comprises a fluoroscopic C-arm.

3. The medical sensor assembly of claim 1, wherein said sensor mount is configured in a front-mount arrangement.

4. The medical sensor assembly of claim 1, wherein said sensor mount is configured in a side-mount arrangement.

5. The medical sensor assembly of claim 1, wherein said spacer is configured to be permanently mounted to said fluoroscopic mount.

6. The medical sensor assembly of claim 5, wherein said sensor engaging element is permanently mounted to said spacer.

7. The medical sensor assembly of claim 6, wherein said sensor engaging element and said spacer form a unibody structure.

8. The medical sensor assembly of claim 1, wherein said sensor engaging element is configured to be permanently mounted to said fluoroscopic mount.

9. The medical sensor assembly of claim 8, wherein said mount engaging element comprises said spacer.

10. The medical sensor assembly of claim 9, wherein said sensor comprises a sensor housing that is permanently mounted to said spacer.

11. The medical sensor assembly of claim 8, wherein said mount engaging element is configured to be removably mounted to said sensor engaging element using a hook-in-loop material.

12. The medical sensor assembly of claim 1, wherein said mount engaging element comprises a sensor housing.

13. The medical sensor assembly of claim 1, wherein said spacer comprises a flange, said sensor engaging element comprises a pair of arms extending from said flange, said mount engaging element comprises a member, and said pair of arms is configured for receiving said member therebetween in a snug relationship.

14. The medical sensor assembly of claim 13, wherein said member comprises a shaft and an enlarged rounded end that is configured to be disposed on said pair of arms when said shaft is inserted between said pair of arms.

15. The medical sensor assembly of claim 13, wherein said pair of arms comprises inwardly curving ends that form an aperture between said pair of arms to receive said member.

16. The medical sensor assembly of claim 13, wherein said inwardly curving ends comprise beveled edges.

17. The medical sensor assembly of claim 13, wherein said pair of arms is not coextensive with said flange.

18. The medical sensor assembly of claim 13, wherein said pair of arms is coextensive with said flange.

19. The medical sensor assembly of claim 13, wherein said flange comprises a concave surface for receiving said member.

20. The medical sensor assembly of claim 13, wherein said member comprises a pair of opposing cutouts, and said pair of arms is configured for engaging said cutouts.

21. The medical sensor assembly of claim 13, wherein said member comprises a sensor housing.

22. The medical sensor assembly of claim 1, wherein said mount engaging element comprises a sensor shaft and a pair of oppositely-extending sensor arms to form a general T-shape, said sensor engaging element comprises a pair of sensor holding arms extending from said spacer, said sensor shaft is configured to be inserted between said pair of sensor holding arms, and said pair of sensor arms is configured to be respectively disposed on said pair of sensor holding arms.

23. The medical sensor assembly of claim 22, wherein said pair of sensor arms is substantially coplanar with said sensor shaft.

24. The medical sensor assembly of claim 22, wherein said pair of sensor arms and said pair of sensor holding arms are mounted to each other in a snap-fit arrangement.

25. The medical sensor assembly of claim 24, wherein said pair of sensor arms and said pair of sensor holding arms respectively comprise ridges and indentations that mate with each other.

26. The medical sensor assembly of claim 22, wherein said pair of sensor arms comprises ends that curve towards said sensor shaft to engage said sensor holding arms.

27. The medical sensor assembly of claim 1, wherein said mount engaging element comprises a member, and said sensor engaging element comprises an open cavity configured to receive said member in a direction substantially perpendicular to a plane in which said sensor mount is mounted.

28. The medical sensor assembly of claim 27, wherein said open cavity is formed in said spacer.

29. The medical sensor assembly of claim 28, wherein said sensor comprises a wire extending therefrom, and said spacer comprises a channel extending from said open cavity to the exterior of said spacer to receive said sensor wire.

30. The medical sensor assembly of claim 27, wherein said open cavity is configured to receive said member in a snap-fit arrangement.

31. The medical sensor assembly of claim 27, wherein said open cavity is substantially circular, and said member is oblong, said member being mounted along the diameter of said circular open cavity.

32. The medical sensor assembly of claim 27, wherein the shape of said open cavity and the shape of said member are substantially similar.

33. The medical sensor assembly of claim 32, wherein the shape of said open cavity and the shape of said member are substantially non-circular.

34. The medical sensor assembly of claim 27, wherein the shape of said open cavity and the shape of said member are hexagonal.

35. The medical sensor assembly of claim 27, wherein each of said open cavity and said member comprises at least two lateral edges that engage each other when said open cavity receives said member.

36. The medical sensor assembly of claim 35, wherein said at least two lateral edges of said member comprise one of ridges or indentations, and said at least two lateral edges of said open cavity comprise another of said ridges or indentations.

37. The medical sensor assembly of claim 27, wherein said cavity has a partially circular cross-sectional shape with a first diameter and an arc extending at least 180 degrees, and said member has a cross-sectional shape with a second diameter substantially similar to said first diameter.

38. The medical sensor assembly of claim 37, wherein said cavity is oblong and comprises a first pair of substantially perpendicular opposing extensions, and said member is oblong and comprises a second pair of substantially perpendicular opposing extension that are configured to be received by said first pair of substantially perpendicular opposing extensions.

39. The medical sensor assembly of claim 27, wherein said member comprises a barb, and said sensor engaging element further comprises a hole formed within said open cavity to receive said barb.

40. The medical sensor assembly of claim 39, wherein said member and said open cavity each have an oblong shape, and said barb extends substantially perpendicular to said member.

41. The medical sensor assembly of claim 27, wherein said member comprises a sensor housing.

42. The medical sensor assembly of claim 1, wherein said mount engaging element comprises a conical member, and said sensor engaging element comprises a conical cavity for receiving said conical member.

43. The medical sensor assembly of claim 42, wherein said conical cavity is formed within said spacer.

44. The medical sensor assembly of claim 43, wherein said sensor comprises a sensor wire extending therefrom, and said spacer comprises a slit configured to receive said sensor wire, said slit extending from said conical cavity to the exterior of said spacer.

45. The medical sensor assembly of claim 44, wherein said slit is oriented substantially parallel to the axis of said conical cavity.

46. The medical sensor assembly of claim 42, wherein said conical member comprises a sensor housing.

47. The medical sensor assembly of claim 46, wherein said non-circular cross-section is D-shaped.

48. The medical sensor assembly of claim 46, wherein said cavity is formed within said spacer.

49. The medical sensor assembly of claim 44, wherein said clip receiving means is configured to receive said clip in a direction parallel to a plane in which said sensor is mounted.

50. The medical sensor assembly of claim 44, wherein said clip receiving means comprises a cavity, said cavity and said clip having matching non-circular cross-sections.

51. The medical sensor assembly of claim 44, wherein said clip receiving means comprises a handle formed on said spacer.

52. The medical sensor assembly of claim 51, wherein said sensor engaging element further comprises a pair of sensor holding arms that extend from said spacer to receive said sensor housing.

53. The medical sensor assembly of claim 44, wherein said clip receiving means comprises an elastomer slit formed in said spacer.

54. The medical sensor assembly of claim 44, wherein said clip receiving means comprises an L-shaped flange formed on said spacer.

55. The medical sensor assembly of claim 44, wherein said clip receiving means comprises a spring clip.

56. The medical sensor assembly of claim 55, wherein said clip receiving means comprises a cutout for receiving said sensor housing.

57. The medical sensor assembly of claim 1, wherein said mount engaging element comprises a sensor housing and a clip disposed thereon, and said sensor engaging element comprises means for receiving said clip.

58. The medical sensor assembly of claim 1, wherein said sensor engaging element comprises one of a member and cavity, said mount engaging element comprises another of said member and cavity, and said member and cavity have substantially uniform and complementary cross-sections, such that said member and said cavity are configured to slidingly engage each other.

59. The medical sensor assembly of claim 58, wherein said member and said cavity slidingly engage each other in a direction substantially parallel to a plane in which said sensor mount is mounted.

60. The medical sensor assembly of claim 58, wherein said sensor engaging element comprises said member, and said mount engaging element comprises said cavity.

61. The medical sensor assembly of claim 58, wherein said sensor engaging element comprises said cavity, and said mount engaging element comprises said member.

62. The medical sensor assembly of claim 58, wherein said one of said member and cavity comprises a protuberance, and said other of said member and cavity comprises an indentation that engages said protuberance when said member is fully engaged within said cavity.

63. The medical sensor assembly of claim 58, wherein said member comprises a key, and said cavity comprises a key slot that engages said key when said member is slidingly engaged within said cavity.

64. The medical sensor assembly of claim 58, wherein said member comprises a detent, and said cavity comprises an aperture that engages said detent when said member is fully engaged with said cavity.

65. The medical sensor assembly of claim 58, wherein said member comprises a pair of opposing slots that substantially extends the length of said member, and said cavity comprises a pair of opposing ridges that substantially extends the length of said cavity.

66. The medical sensor assembly of claim 58, wherein said complementary cross-sections are T-shaped.

67. The medical sensor assembly of claim 58, wherein said complementary cross-sections are ellipsoidal.

68. The medical sensor assembly of claim 67, wherein said ellipsoidal complementary cross-sections each comprise lateral opposing extensions.

69. The medical sensor assembly of claim 58, wherein said complementary cross-sections are trapezoidal.

70. The medical sensor assembly of claim 58, wherein said complementary cross-sections are rectangular.

71. The medical sensor assembly of claim 58, wherein said sensor comprises a finger handle.

72. The medical sensor assembly of claim 58, wherein said mount engaging element comprises a sensor housing.

73. The medical sensor assembly of claim 1, wherein said sensor engaging element comprises one of a first matching snap protuberance and a snap hole, said mount engaging element comprises another of said first matching snap protuberance and snap hole, and said first matching snap hole and said first matching snap protuberance are configured to respectively snap together.

74. The medical sensor assembly of claim 73, wherein said one of a snap protuberance and snap hole comprises a snap protuberance, and said other one of a snap protuberance and a snap hole comprises a snap hole.

75. The medical sensor assembly of claim 73, wherein said sensor engaging element comprises one of a second matching snap protuberance and a snap hole, said mount engaging element comprises another of said second matching snap protuberance and snap hole, and said second matching snap hole and said snap protuberance are configured to respectively snap together.

76. The medical sensor assembly of claim 75, wherein said one of said first matching snap protuberance and a snap hole and said one of said second matching snap protuberance and a snap hole each comprises a snap protuberances, said other of said first matching snap protuberance and a snap hole and said other of said second matching snap protuberance and a snap hole each comprises a snap hole.

77. The medical sensor assembly of claim 1, wherein said sensor comprises a sensor housing, said mount engaging element comprises a rigid planar member, said sensor engaging element comprises a flexible planar member that is configured to be removably attached to said spacer when said rigid planar member is disposed on said spacer, and said sensor engaging element comprises an aperture through which said sensor housing can fit, but through which said rigid planar member cannot fit.

78. The medical sensor assembly of claim 77, wherein said flexible planar member is configured to be removably mounted to said spacer using a hook-in-loop material.

79. A medical sensor assembly for use with a fluoroscopic mount, comprising:
an electromagnetic sensor configured for outputting positional data relating to said fluoroscopic mount, said sensor comprising a mount engaging element; and
a sensor mount composed of a non-ferromagnetic material, said sensor mount comprising a spacer and a sensor engaging element, wherein said sensor engaging element and said mount engaging element are removably mounted in an interference relationship with each other, and said spacer is configured to maintain a prescribed distance between said sensor and said fluoroscopic mount.

80. The medical sensor assembly of claim 79, wherein said fluoroscopic mount comprises a fluoroscopic C-arm.

81. The medical sensor assembly of claim 79, wherein said sensor mount is configured in a front-mount arrangement.

82. The medical sensor assembly of claim 79, wherein said sensor mount is configured in a side-mount arrangement.

83. The medical sensor assembly of claim 79, wherein said spacer is configured to be permanently mounted to said fluoroscopic mount.

84. The medical sensor assembly of claim 83, wherein said sensor engaging element is permanently mounted to said spacer.

85. The medical sensor assembly of claim 84, wherein said sensor engaging element and said spacer form a unibody structure.

86. The medical sensor assembly of claim 79, wherein said sensor engaging element is configured to be permanently mounted to said fluoroscopic mount.

87. The medical sensor assembly of claim 86, wherein said spacer is removably mounted to said sensor engaging element.

88. The medical sensor assembly of claim 87, wherein said mount engaging element is permanently mounted to said spacer.

89. The medical sensor assembly of claim 86, wherein said spacer is removably mounted to said sensor engaging element using a hook-in-loop material.

90. The medical sensor assembly of claim 79, wherein said mount engaging element comprises a sensor housing.

91. A medical image-acquisition device, comprising:
a fluoroscopic mount;
an electromagnetic sensor configured for outputting positional data relating to said fluoroscopic mount, said sensor comprising a mount engaging element; and
a sensor mount composed of a non-ferromagnetic material, said sensor mount comprising a spacer and a sensor engaging element, wherein said sensor engaging element and said mount engaging element are removably mounted in an interference relationship with each other, and said spacer is configured to maintain a prescribed distance between said sensor and said fluoroscopic mount.

92. The medical image-acquisition device of claim 91, wherein said fluoroscopic mount comprises a fluoroscopic C-arm.

93. The medical image-acquisition device of claim 91, wherein said sensor mount is configured in a front-mount arrangement.

94. The medical image-acquisition device of claim 91, wherein said sensor mount is configured in a side-mount arrangement.

95. The medical image-acquisition device of claim 91, wherein said spacer is permanently mounted to said fluoroscopic mount.

96. The medical image-acquisition device of claim 95, wherein said sensor engaging element is permanently mounted to said spacer.

97. The medical image-acquisition device of claim 96, wherein said sensor engaging element and said spacer form a unibody structure.

98. The medical image-acquisition device of claim 91, wherein said sensor engaging element is permanently mounted to said fluoroscopic mount.

99. The medical image-acquisition device of claim 98, wherein said spacer is removably mounted to said sensor engaging element.

100. The medical image-acquisition device of claim 99, wherein said mount engaging element is permanently mounted to said spacer.

101. The medical image-acquisition device of claim 98, wherein said spacer is removably mounted to said sensor engaging element using a hook-in-loop material.

102. The medical image-acquisition device of claim 91, wherein said mount engaging element comprises a sensor housing.

* * * * *